US006911527B1

(12) United States Patent
Scala et al.

(10) Patent No.: US 6,911,527 B1
(45) Date of Patent: Jun. 28, 2005

(54) HIV RELATED PEPTIDES

(75) Inventors: Giuseppe Scala, Pozzuoli (IT); Xueni Chen, Ann Arbor, MI (US); Oren J. Cohen, Bethesda, MD (US); Anthony S. Fauci, Washington, DC (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/869,003

(22) PCT Filed: Jan. 7, 2000

(86) PCT No.: PCT/US00/00372

§ 371 (c)(1),
(2), (4) Date: Sep. 25, 2001

(87) PCT Pub. No.: WO00/42068

PCT Pub. Date: Jul. 20, 2000

Related U.S. Application Data

(60) Provisional application No. 60/132,760, filed on May 6, 1999, and provisional application No. 60/115,430, filed on Jan. 11, 1999.

(51) Int. Cl.[7] ................................................ A61K 38/04

(52) U.S. Cl. ....................... 530/328; 530/323; 530/324; 530/325; 530/326; 530/327; 530/826; 435/5; 435/7.1; 424/188.1; 424/199.1; 424/208.1

(58) Field of Search ........................... 424/188.1, 199.1, 424/208.1; 435/5, 7.1; 530/328, 323–327, 226

(56) References Cited

FOREIGN PATENT DOCUMENTS

| | | | |
|---|---|---|---|
| EP | 0471407 | A2 | 2/1992 |
| EP | 0673948 | A1 | 9/1995 |
| WO | 91/09872 | A3 | 7/1991 |
| WO | 94/02614 | A1 | 2/1994 |
| WO | 94/02626 | A1 | 2/1994 |
| WO | 99/66046 | A1 | 12/1999 |
| WO | 99/66957 | A2 | 12/1999 |
| WO | 99/66957 | * | 12/1999 |

OTHER PUBLICATIONS

Riffkin et al. "A Single amino–acid change between the antigenically different extracellular serine proteases V2 and B2 from *Dichelobacter nodosus", Gene*, vol. 167 (1995), pp. 279–283.*

Abaza et al. "Effects of amino acid substitutions outside an antigenic site on protein binding to monoclonal antibodies of predetermined specificity obtained by peptide immunization", *Journal of Protein Chemistry*, vol. 11, No. 5 (1992), pp. 433–444.*

Cruse et al. *Illustrated Dictionary of Immunology* (Boca Raton, FL, CRC Press, Inc., 1995), p. 309. QR180.4.C78.*

Paul, *Fundamental Immunology*, (Philadelphia & New York, Lippincott–Raven Publishers, 1993), pp. 250 and 1311–1312. QR181.F84.*

Feinberg et al. "AIDS vaccine models: Challenging challenge viruses" Nature Medicine, vol. 8, No. 3(Mar. 2002), pp. 207–210.*

Nath et al. "The Chimpanzee and other non–human–primate models in HIV–1 vaccine research", Trends in Microbiology, vol. 8, No. 9(2000), pp. 426–431.*

Bonnycastle, et al.; "The Identification of "HIV–1–mimic" Peptides Using Antibodies from the Sera of HIV–1 Infected, Long–Term Non–Progressors;"*Conf Adv AIDS Vaccine Dev*; May 4–7, 1997; p. 109; United States.

Boots, et al.; "Anti–Human Immunodeficiency Virus Type 1 Human Monoclonal Antibodies that Bind Discontinuous Epitopes in the Viral Glycoproteins Can Identify Mimotopes from Recombinant Phage Peptide Display Libraries;" *AIDS Research and Human Retroviruses*; 1997; vol. 13; No. 18; Mary Ann Liebert, Inc.

Buchbinder, et al.; "HIV–Infected Long–Term Nonprogressors: Epidemiology, Mechanisms of Delayed Progression, and Clinical and Research Implications;" *Microbes and Infection*; Nov. 1999; pp. 1113–1120; vol. 1.

Cotropia, et al.; "A Human Monoclonal Antibody to HIV–1 gp41 With Neutralizing Activity Against Diverse Laboratory Isolates;" *Journal of Acquired Immune Deficiency Syndromes and Human Retrovirology*; 1996; pp. 221–232; vol. 12; Lippincott–Raven Publishers; Philadelphia.

D'Souza et al.; "Evaluation and Monoclonal Antibodies to Human Immunodeficiency Virus Type 1 Primary Isolates by Neutralization Assays: Performance Criteria for Selecting Candidate Antibodies for Clinical Trials;" *The Journal of Infectious Diseases*; 1997; pp. 1056–1062; vol. 175.

Felici, et al; "Selection of Antibody Ligands from a Large Library of Oligopeptides Expressed on a Multivalent Exposition Vector;" *Journal of Molecular Biology*; 1991; pp. 301–310; No. 2; Academic Press Limited; London, Great Britain.

Haesevelde, et al.; "Genomic Cloning and Complete Sequence Analysis of a Highly Divergent African Human Immunodeficieny Virus Isolate;" *Journal of Virology*; Mar. 1994; pp. 1586–1596; vol. 68; No. 3; American Society for Microbiology.

(Continued)

*Primary Examiner*—Jeffrey Stucker
(74) *Attorney, Agent, or Firm*—Townsend and Townsend and Crew

(57) ABSTRACT

This invention is the discovery of novel specific epitopes and antibodies associated with long term survival of HIV-1 infections. These epitopes and antibodies have use in preparing vaccines for preventing HIV-1 infection or for controlling progression to AIDS.

7 Claims, 10 Drawing Sheets

OTHER PUBLICATIONS

Hogervorst, et al.; "Predictors for Non–and Slow Progression in Human Immodeficiency Virus (HIV) Type 1 Infection: Low Viral RNA Copy Numbers in Serum and Maintenance of High HIV–1 p24–Specific but Not V3–Specific Antibody Levels;" *The Journal of Infectious Diseases*; 1995; pp. 811–821; vol. 171; The University of Chicago.

Ida, et al; "HIV Type 1 V3 Variation Dynamics in Vivo: Long–Term Persistence of Non–Syncytium–Inducing Genotypes during the Course of Progressive AIDS;" *AIDS Research and Human Retroviruses*; 1997; pp. 1597–1609; vol. 13, No. 18; Mary Ann Liebert, Inc.

Montefiori, et al.; Neutralizing and Infection–Enhancing Antibody Responses to Human Immunodeficiency Virus Type 1 in Long–Term Nonprogressors; *The Journal of Infectious Diseases*; 1996; pp. 60–87; vol. 173; The University of Chicago.

Pantaleo et al.; "Studies in Subjects with Long–Term Nonprogressive Human Immunodeficiency Virus Infection;" *Long–Term Nonprogressive HIV Infection*; Jan. 26, 1995; pp. 209–216; vol. 332; No. 4; The New England Journal of Medicine.

Rusconi, et al.; "Patterns of in Vitro Anti–Human Immunodeficiency Virus Type 1 Antibody Production in Long–Term Nonprogressors;"*Clinical Immunology and Immunopathology*; Dec. 1997; pp. 320–323; vol. 85; No. 3; Academic Press.

Toran, et al. Molecular Analysis of HIV–1 gp120 Antibody Response using Isotype IgM and IgG phage display libraries from a Long–Term Non–Progressor HIV–1–Infected Individual; *Eur. J. Immunol*; 1999; pp. 2666–2675; vol. 29; Wiley–VCH Verlag GmbH; Weinheim.

Veronese, et al; "Structural Mimicry and Enhanced Immunogenicity of Peptide Epitopes Displayed on Filamentous Bacteriophage The V3 Loop of HIV–1 gp120;" *J. Mol Biol.*; 1994; pp. 167–172; vol. 243; Academic Press Limited.

* cited by examiner

| SELECTION | CLONE | SHIV NEGATIVE | | | MONKEY SERA | | | | SHIV POSITIVE | | | | |
|---|---|---|---|---|---|---|---|---|---|---|---|---|---|
| | | B042 | B027 | B118 | B047 | A125 | 42C | E50 | AK98 | 4150 | 79 | 4138 | 17860 | 17846 |
| 1 | p195 | – | – | – | – | ▨ | ▨ | – | – | – | ▨ | ▨ | ▨ | ▨ |
| | p197 | – | – | – | – | – | – | – | – | – | ▨ | ▨ | – | ▨ |
| | p217 | – | – | – | – | ▨ | ▨ | – | – | – | ▨ | ▨ | ▨ | ▨ |
| | p287 | – | – | – | – | ▨ | – | ▨ | – | ▨ | ▨ | ▨ | ▨ | ▨ |
| | p335 | – | – | – | – | – | ▨ | – | – | – | – | – | – | – |
| 2 | p32 | – | – | – | – | – | ░ | ░ | – | – | – | – | – | – |
| | p54 | – | – | – | – | – | – | – | – | – | – | – | – | – |
| | p163 | – | – | – | – | – | – | – | – | – | – | – | – | – |
| | p483 | – | – | – | – | – | ░ | – | – | – | – | – | – | – |
| | p689 | – | – | – | – | – | – | – | – | – | – | – | – | – |

HIV RELATED PEPTIDES

CROSS-REFERENCES TO RELATED APPLICATIONS

This application claims priority to U.S. Provisional Application Ser. No. 60/115,430 filed on Jan. 11, 1999 and to U.S. Provisional Application Ser. No. 60/132,760 filed on May 6, 1999 each of which is incorporated by reference herein.

STATEMENT AS TO RIGHTS TO INVENTIONS MADE UNDER FEDERALLY SPONSORED RESEARCH AND DEVELOPMENT

Not Applicable

BACKGROUND OF THE INVENTION

Efforts to develop a protective human immunodeficiency virus-1 (HIV-1) vaccine have been hindered by difficulties in identifying epitopes capable of inducing broad neutralizing antibody responses. The high mutation rate that occurs in HIV-1 envelope proteins and the complex structure of gp120 as an oligomer associated with gp41 results in a high degree of antigenic polymorphism. To overcome these obstacles, we have identified antigenic and immunogenic mimics of HIV-1 epitopes that are specific to HIV-resistant individuals. The epitope mimics were identified by screening random peptide libraries using sera from HIV-infected subjects who were long term non-progressors (LTNPs). After extensive counter-screening with HIV-negative sera, we isolated peptides specifically recognized by antibodies from HIV-1 infected individuals.

SUMMARY OF THE INVENTION

The present invention includes an antigenic peptide of less than 100 amino acids having an antigenic subsequence selected from the group consisting of X-KSSGKLISL-X (SEQ ID NO:1), X-CNGRLYCGP-X (SEQ ID NO:2)and X-GTKLVCFAA-X (SEQ ID NO:3), wherein X is independently an amino acid or sequence of amino acids with the proviso that X is not identical to the amino acid or amino acids naturally flanking the corresponding subsequences in HIV-1.

An additional embodiment of this invention is a vaccine for protecting against HIV-1 infection comprising an antigenic peptide of less than 100 amino acids having an antigenic subsequence selected from the group consisting of X-KSSGKLISL-X (SEQ ID NO:1), X—CNGRLYCGP-X (SEQ ID NO:2) and X-GTKLVCFAA-X (SEQ ID NO:3), wherein X is independently an amino acid or sequence of amino acids with the proviso that X is not identical to the amino acid or amino acids naturally flanking the subsequences in HIV-1.

Embodiments of the present invention also include a composition for raising antibodies against HIV-1, said composition comprising an antigenic determinant selected from the group consisting of KSSGKLISL (SEQ ID NO:4), CNGRLYCGP (SEQ ID NO:5) and GTKLVCFAA (SEQ ID NO:6), wherein the composition does not give rise to HIV-specific antibodies to more than eight other antigenic determinants on HIV-1.

A further embodiment of this invention is a vaccine for protecting against HIV-1, said vaccine comprising an antigenic determinant selected from the group consisting of KSSGKLISL (SEQ ID NO:4), CNGRLYCGP (SEQ ID NO:5) and GTKLVCFAA (SEQ ID NO:6), wherein the composition does not give rise to HIV-specific antibodies to more than eight other antigenic determinants on HIV-1.

The present invention also encompasses a method for raising antibodies against HIV-1, said method comprising administering to an animal competent to raise antibodies an amount of a composition comprising an antigenic determinant selected from the group consisting of KSSGKLISL (SEQ ID NO:4), CNGRLYCGP (SEQ ID NO:5) and GTKLVCFAA (SEQ ID NO:6), wherein the composition does not give rise to HIV-specific antibodies to more than eight other antigenic determinants on HIV-1, said amount sufficient to raise antibodies in the animal.

An additional embodiment of the invention comprises binding proteins which specifically bind to a peptide selected from the group consisting of: KSSGKLISL (SEQ ID NO:4), CNGRLYCGP (SEQ ID NO:5) and GTKLVCFAA (SEQ ID NO:6). A preferred embodiment comprises a binding protein wherein the protein is an antibody.

An alternative embodiment of the invention comprises an antibody which specifically binds to a peptide sequence selected from the group consisting of: KSSGKLISL (SEQ ID NO:4), CNGRLYCGP (SEQ ID NO:5) and GTKLVCFAA (SEQ ID NO:6). Variants of antibodies (including an antigen binding site), such as chimeric antibodies, humanized antibodies, veneered antibodies, and recombinantly engineered single chain antibodies which bind to the peptides of the present invention are included within the scope of the invention.

The invention additionally includes a method for inducing passive immunity in a host against HIV-1 comprising the step of administering an amount of antibody which specifically binds to a protein selected from the group consisting of: KSSGKLISL (SEQ ID NO:4), CNGRLYCGP (SEQ ID NO:5) and GTKLVCFAA (SEQ ID NO:6) said amount sufficient to induce passive immunity against HIV-1.

An alternative embodiment comprises a method for detecting HIV-1 in biological samples said method comprising detecting the presence of HIV-1 in a sample with an antibody which specifically binds to a protein selected from the group consisting of: KSSGKLISL (SEQ ID NO:4), CNGRLYCGP (SEQ ID NO:5) and GTKLVCFAA (SEQ ID NO:6) in an amount sufficient to detect the presence of HIV-1 in a sample.

A further embodiment of the invention comprises a method for detecting HIV-specific antibodies in a person suspected of being infected with HIV-1 said method comprising the step of incubating a biological sample from the person with an antigenic determinant selected from the group consisting of KSSGKLISL (SEQ ID NO:4), CNGRLYCGP (SEQ ID NO:5) and GTKLVCFAA (SEQ ID NO:6) in an amount sufficient to detect the presence of antibodies which bind to the antigenic determinant.

Other embodiments of the invention include a method for selecting for antibodies specific to patients with long term nonprogression (LTNP) into AIDS said method comprising: (a) screening serum from LTNP patients for HIV specific antibodies and comparing the antibodies to patients with AIDS.

Further, the invention includes peptides specific to antibodies from patients with long term nonprogression (LTWP) into AIDS said peptides generated via a method comprising: (a) screening serum from LTNP patients for HIV-specific antibodies, and; (b) comparing the antibodies to patients with AIDS.

An alternative embodiment comprises phagotopes having peptides exhibiting antigens specific to antibodies found in patients with long term nonprogression (LTNP) into AIDS.

Also included in the invention is an embodiment comprising phagotopes having peptides exhibiting antigens specific to antibodies found in patients with long term nonprogression (LTNP) into AIDS said phagotopes produced by screening serum from LTNP patients for HIV-specific antibodies against a random library of phagotopes, and; (b) comparing the antibodies to patients with AIDS.

A further embodiment of the invention comprises an antigenic peptide of less than 100 amino acids having an antigenic subsequence selected from the group consisting of EATVVYPAP (SEQ ID NO:7), TKTLIYGGA (SEQ ID NO:8), KRIVIGPQT (SEQ ID NO:9), CCGCLTCSV (SEQ ID NO:10), SGRLYCHESW (SEQ ID NO:11), FALSHYDKP (SEQ ID NO:12), and RPTLRFQGA (SEQ ID NO:13).

Embodiments of the invention also include a vaccine for protecting against HIV-1 infection comprising an antigenic peptide of less than 100 amino acids having an antigenic subsequence selected from the group consisting of EATVVYPAP (SEQ ID NO:7), TKTLIYGGA (SEQ ID NO:8), KRIVIGPQT (SEQ ID NO:9), CCGCLTCSV (SEQ ID NO: 10), SGRLYCHESW (SEQ ID NO: 11), FALSHYDKP (SEQ ID NO: 12), and RPTLRFQGA (SEQ ID NO:13).

An additional embodiment of the invention comprises an antigenic peptide of less than 100 amino acids having an antigenic subsequence selected from the group consisting of EGEFCKSSGKLISLCGDPAK (SEQ ID NO: 14), EGEFCQTKLVCFAAAGDPAK (SEQ ID NO:15), EGEFCCNGRLYCQPCGDPAK (SEQ ID NO: 16), EGEFCCAGQLTCSVCGDPAK (SEQ ID NO: 17), CSGRLYCHESWC (SEQ ID NO: 18), and TKTLIYQGA (SEQ ID NO: 19).

The invention also includes a vaccine for protecting against HIV-1 infection comprising an antigenic peptid of less than 100 amino acids having an antigenic subsequence selected from the group consisting of EGEFCKSSGKLISLCGDPAK (SEQ ID NO: 14), EGEFCQTKLVCFAAAGDPAK (SEQ ID NO:15), EGEFCCNGRLYCQPCGDPAK (SEQ ID NO:16), EGEFCCAGQLTCSVCGDPAK (SEQ ID NO:17), CSGRLYCHESWC (SEQ ID NO:18), and TKTLIYQGA (SEQ ID NO:19).

A further diagnostic embodiment includes the use of peptides of the invention to determine prognosis or disease progression in persons with chronic diseases or infections.

As will be apparent from the discussion below, other methods and embodiments are also contemplated.

DETAILED DESCRIPTION

Introduction

Figure 1A:
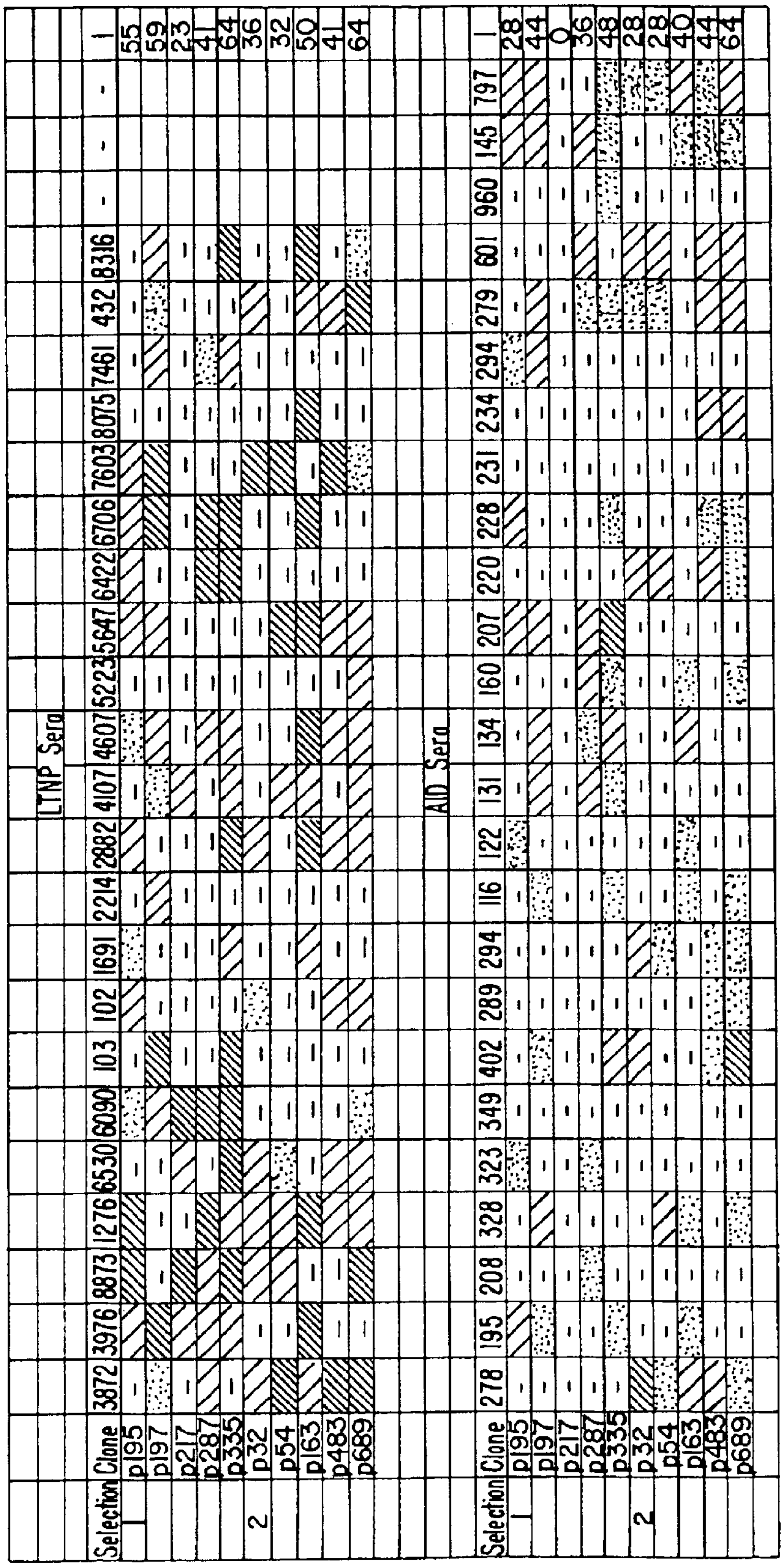
FIG. 1. ELISA reactivities of HIV-specific phagotopes. a, LTNP and AIDS subjects were selected as reported (Pantaleo et al., *N. Engl. J Med* 332:209 (1995)). HIV-specific phagotopes were identified from RPL pVIII9aa-cys (selection 1), or pVIII9aa (selection 2) by serial steps of screening and phage colony purification as described in the Methods section. Results are expressed as fold increase of the average values of the phagotopes over values of the wild-type phages. Values were considered positive when at least four-fold higher than the background signal of wild-type phage. Average values of at least four independent assays are shown as □<4; 4<▒<10; 10.1<▒<20; ■>20. The far right column indicates the recognition frequency of positive sera by each phagotope (f). The percentages of significant phage reactivity in the HIV-positive and control groups were compared using the Fisher Exact Test; p values (p<0.001) were adjusted for multiple testing using the Bonferroni method. b, Comparison of ELISA reactivities of phagotopes with sera of LTNP (hatched bars) versus AIDS subjects (black bars). Data are expressed as mean±SEM of fold increase for each phagotope. Statistical analysis was performed according to the one-sided Student's t test; asterisks indicate p<0.05.

This invention provides for peptides and antibodies which are associated with long term survival of persons infected with HIV-1. Immunogenic peptides are identified herein and are correlated with HIV-specific proteins. Other immunogenic peptides are conformational equivalents of epitopes on HIV-1 proteins and have little amino acid identity to known HIV-1 proteins. The following teaches those of skill how to make and use the peptides of this invention.

Definitions

Binding Protein: A binding protein is a protein which binds specifically to a target ligand. The term includes both antibodies and proteins generated by random selection such as those displayed on phage.

Antibody: As used herein, an "antibody" refers to a protein functionally defined as a binding protein and structurally defined as comprising an amino acid sequence that is recognized by one of skill as being derived from the framework region of an immunoglobulin encoding gene of an animal producing antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the $(Fab')_2$ dimer into an Fab' monomer. The Fab' monomer is essentially an Fab with part of the hinge region (see, e.g., *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker. Huston et al., *Proc. Nat. Acad. Sci. USA* 85:5879–5883 (1988). While the VH and VL are connected to each as a single polypeptide chain, the VH and VL domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see, e.g., U.S. Pat. Nos. 5,091,513; 5,132,405; and 4,956,778). Particularly preferred antibodies include all those that have been displayed on phage (e.g., scFv, Fv, Fab and disulfide linked Fv (Reiter et al., *Protein Eng.,* 8:1323–1331 (1995)). Antibodies can also include diantibodies and miniantibodies.

Antibody Combining Site: An antibody combining site is that structural portion of an antibody molecule comprised of a heavy and light chain variable and hypervariable regions that specifically binds (immunoreacts with) an antigen. The term immunoreact in its various forms means specific binding between an antigenic determinant-containing molecule and a molecule containing an antibody combining site such as a whole antibody molecule or a portion thereof.

Antigenic: Antigenic refers to the ability of a composition to give rise to antibodies specific to itself or to give rise to a cell-mediated immune response.

Antigenic determinant: An antigenic determinant or epitope is the site of recognition or binding of an antibody to its target or the site of recognition or binding of a T cell receptor. It is minimally defined by 4–6 amino acids. It can be linear or conformational.

Phagotope: A peptide displayed on phage bound by serum antibodies.

Monoclonal Antibody: A monoclonal antibody in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, erg., a bispecific monoclonal antibody.

Fusion Polypeptide: A polypeptide comprised of at least two polypeptides and a linking sequence to operatively link the two polypeptides into one continuous polypeptide. The two polypeptides linked in a fusion polypeptide are typically derived from two independent sources, and therefore a fusion polypeptide comprises two linked polypeptides not normally found linked in nature.

Synthetic peptide: A peptide that is not naturally occurring, but is man-made using methods such as chemical synthesis or recombinant DNA technology.

Vaccines: Vaccines refer to compositions or mixtures that when introduced into the circulatory system of an animal will evoke a protective response to a pathogen. Vaccines can be either passive or active. Vaccines are passive when they include immunoglobulins which confer protection and are active when they elicit from the host antibodies which are protective against a pathogen.

Method for identifying antibodies specific to persons resistant to disease progression.

Persons harboring infectious agents that are initially dormant and then progress into clinical disease states present a problem to clinicians. Persons who do not rapidly progress to the clinical state are considered resistant. Often the reason for a person's resistance is unknown but the immune system is thought to play a part in the delay of clinical manifestations of the disease. HIV-1 infection is a classic example of this phenomenon, but other diseases such as *Herpes simplex* and *Herpes zoster* infections, lyme disease, infection with the hepatitis viruses, and tuberculosis follow this general pattern.

To identify antibodies specific to resistance one simply collects a representative sample of the antibodies in healthy, chronically infected and acutely infected persons. The antibodies are then screened and comparisons made to determine the unique antibodies to the pathogens that are present in the resistant persons. There are numerous means to achieve this which would be immediately apparent to those of skill once the importance of the selection of resistant persons is noted as it was in the instant situation with HIV-1.

More particularly, one immobilizes the antibodies from infected persons and independently creates a random peptide library using any number of means including synthetic peptide chemistry, phage display technology, and other virally based peptide display technology. Methods for the production of phage display libraries, including vectors and methods of diversifying the population of peptides which are expressed, are well known in the art. (See, for example, Smith and Scott, *Methods Enzymol.* 217:228–257 (1993); Scott and Smith, *Science* 249:386–390 (1990); and Huse, WO 91/07141 and WO 91/07149. Cyclic peptide libraries also are well known in the art (see, for example, Koivunen et al., *Methods Enzymol.* 245:346–369 (1994)). These or other well known methods can be used to produce a phage display library The library is blocked by contact with non-immobilized antibodies from healthy sera, or selectively screened for disease-specific peptides using an immunoaffinity column prepared with healthy sera and the eluant subsequently used for further selection. In either case, the disease-enriched library is then contacted with immobilized antibodies from resistant persons or from acutely infected persons and the two populations of antibodies are contrasted using conventional technology to identify the antibodies that are specifically found in the sera of resistant individuals.

Alternatively, a strategy based on positive selection may be employed wherein a pool of clones bound by serum antibodies from a single resistant (or acutely infected) person is identified using an immunoaffinity column. The pool of clones is then individually screened for those clones that react with a second, different serum from a person of the same disease status as that of the source of the first serum. The positive clones identified with the second serum are then analyzed for their frequency and selectivity of reaction with sera from resistant or acutely infected persons and healthy persons using conventional techniques such as ELISA.

In the example section, one procedure is provided; however, those of skill should recognize that a number of variations on this procedure will lead to the identification of antibodies and antigens that are specific to those persons demonstrating long term resistance to a disease or infection.

Manufacture of Reptides for raising HIV-specific antibodies

The peptides of the invention can be prepared in a wide variety of ways. The peptides can be synthesized in solution or on a solid support in accordance with conventional techniques. Various automatic synthesizers are commercially available and can be used in accordance with known protocols. See, for example, Stewart & Young, SOLID PHASE PEPTIDE SYNTHESIS, 2D. ED., Pierce Chemical Co. (1984).

Alternatively, recombinant DNA technology may be employed wherein a nucleotide sequence which encodes a peptide of interest is inserted into an expression vector, transformed or transfected into an appropriate host cell and cultivated under conditions suitable for expression. It will be understood by those of skill in the art that peptide compositions containing multiple peptides may be produced by engineering a nucleic acid sequence to encode a fusion protein comprising the multiple peptide sequences. These procedures are generally known in the art, as described generally in, for example, Sambrook et al., MOLECULAR CLONING, A LABORATORY MANUAL, Cold Spring Harbor Press, Cold Spring Harbor, N.Y. (1989).

Expression vectors suitable for use in the present invention may comprise at least one expression control element operationally linked to the nucleic acid sequence. Expression control elements are inserted in the vector to control and regulate the expression of the nucleic acid sequence. Additional preferred or required operational elements include, but are not limited to, a leader sequence, termination codons, polyadenylation signals, and any other sequences necessary or preferred for the appropriate transcription and subsequent translation of the nucleic acid sequence in the host system. It will be understood by one skilled in the art the correct combination of required or preferred expression control elements will depend on the host system chosen. It will further be understood that the expression vector should contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (see, e.g., Ausubel et al. in "Current Protocols in Molecular Biology", John Wiley and Sons, New York, N.Y. (1987)) or are commercially available.

Modification of Peptides

With regard to protein based vaccines of the invention, there are a number of strategies for amplifying an immunogen's effectiveness, particularly as related to the art of vaccines. These include strategies whereby an immunogenic peptide may be directly modified to enhance immunogenicity or physical properties such as stability. For example, cyclization or circularization of a peptide can increase the peptide's antigenic and immunogenic potency. See, e.g., U.S. Pat. No. 5,001,049 which is incorporated by reference herein.

The immunogenicity of the peptides of the present invention may also be modulated by coupling to fatty acid moieties to produce lipidated peptides. Convenient fatty acid moieties include glycolipid analogs, N-palmityl-S2RS)2,3-bis-(palmitoyloxy)pmopyl-cysteinyl-serine (PAM3 Cys-Ser), N-palmityl-S-[2,3 bis (palmitoyloxy)-(2RS)-propyl-[R]-cysteine (TPC) or adipalmityl-lysine moiety The peptides may also be conjugated to a lipidated amino acid, such as an octadecyl ester of an aromatic acid, such as tyrosine, including actadecyl-tryrosine (OTH).

Protein Analogs

Protein analogs are defined functionally as those compounds that will act chemically and biologically as the peptides provided herein. In particular the invention includes analogs which bind with fidelity to the antibodies which are generated using the peptides described herein. The analogs will find advantage as more stable and as having longer half life under in vivo conditions. In addition, it may also be advantageous to modify the peptides in order to impose a conformational restraint upon it. This may be useful, for example, to mimic a naturally-occurring conformation of the peptide in the context of the native protein in order to optimize the effector immune responses that are elicited. Modified peptides are referred to herein as "analog" peptides. The term "analog" extends to any functional and/or structural equivalent of a peptide characterized by its increased stability and/or efficacy in vivo or in vitro in respect of the practice of the invention. The term "analog" also is used herein to extend to any amino acid derivative of the peptides as described herein.

Analogs of the peptides contemplated herein include, but are not limited to, modifications to side chains; and incorporation of unnatural amino acids and/or their derivatives, non-amino acid monomers and cross-linkers. Other methods which impose conformational constraint on the peptides or their analogs are also contemplated.

It will be apparent that the peptide of the invention can be modified in a variety of different ways without significantly affecting the functionally important immunogenic behavior thereof. Possible modifications to the peptide sequence may include the following:

One or more individual amino acids can be substituted by amino acids having comparable or similar properties, thus, for example,:

V may be substituted by I;
T may be substituted by S;
K may be substituted by R; and
L may be substituted by I, V or M.

One or more of the amino acids of the peptides of the invention can be replaced by a "retro-inverso" amino acid, i.e., a bifunctional amine having a functional group corresponding to an amino acid, as discussed in WO 91/13909

One or more amino acids can be deleted or added. Added amino acids may, for example, comprise residues that correspond to phage coat protein sequences that are adjacent to the phagotope sequence.

Structural analogs mimicking the 3-dimensional structure of the peptide can be used in place of the peptide itself.

Examples of side chain modifications contemplated by the present invention include modification of amino groups, such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6, trinitrobenzene sulfphonic acid (TNBS); acylation of amino groups with succinic anhydride and tetrahydrophthalic anhydride; and pyridoxylation of lysine with pyridoxal-5'-phosphate followed by reduction with $NaBH_4$.

The guanidino group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivatization, for example, to a corresponding amide.

Sulfhydryl groups may be modified by methods such as carboxy-methylation with iodoacetic acid or iodoacetamide; performic acid oxidation to cysteic acid; formation of mixed disulphides with other thiol compounds; reaction with maleimide, maleic anhydride or other substituted maleimide; formation of mercurial derivatives using 4-chloromercur-ibenzoate, 4-chloromercuriphenylsulfonic acid, phenylmercury chloride, 2-chloromercuric-4-nitrophenol and other mercurials; and carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tryosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4amino-3-hydroxy-5-phenylpentanoic acid, 6-aminohexanoic acid, t-butyglycine, norvaline, phenylglycine, ornithine, sarcosine, 4-amino-3-hydroxy-6-methylheptanoic acid, 2-thienylalanine, and/or D-isomers of amino acids.

Crosslinkers can be used, for example, to stabilize 3-dimensional conformations, using homo-bifunctional crosslinkers such as the bifunctional imido esters having (CH2)[n], spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio (for SH) or carbodiimide (for COOH). In addition, peptides could be conformationally constrained by, for example, incorporation of alpha-methylamino acids, introduction of double bonds between adjacent C atoms of amino acids and the formation of cyclic peptides or analogs by introducing covalent bonds such as forming an amide bond between N and C termini, between two side chains or between a side chain and the N or C terminus.

Conjugation to other peptides or polypeptides

The peptides of the invention or their analogs may occur as a single length or as multiple tandem or non-tandem repeats. A single type of peptide or analog may form the repeats or the repeats may be composed of different molecules including a suitable carrier.

The use of the peptides provided herein under in viva conditions may require their chemical modification since the peptides themselves may not have a sufficiently long scrum and/or tissue half-life. For this purpose, the peptides may optionally be linked to a carrier molecule, possibly via chemical groups of amino acids of the peptide or via additional amino acids added at the C- or N-terminus.

A small peptide antigen can be conjugated to a suitable carrier, usually a protein molecule, to enhance its immunogenicity. This procedure has several facets. It can allow multiple copies of an antigen, such as a peptide, to be conjugated to a single larger carrier molecule. Additionally, the carrier may possess properties which facilitate transport, binding, absorption or transfer of the antigen. The conjugation between a peptide and a carrier can be accomplished using one of the methods known in the art. Specifically, conjugation can be performed using bifunctional cross-linkers as binding agents as detailed, for example, by Means and Feeney, *Bioconjugate Chem.* 1:2–12 (1990). Many suitable linkages are known, e.g., using the side chains of Tyr residues. Suitable carriers are well known in the art, and include, e.g., keyhole limpet hemocyanin (KLH), thyroglobulin, serum albumin, purified protein derivative of tuberculin (PPD), ovalbumin, tetanus toxoid, non-protein carriers and many others.

The immunogenicity of the peptide compositions of the present invention may further be enhanced by linking the peptides to one or more peptide sequences that are able to a elicit a cellular immune response (see, e.g., WO94/20127). Peptides that stimulate cytotoxic T-lymphocyte (CTL) responses as well as peptides that stimulate helper T lymphocyte (HTL) responses are useful for linkage to the peptides of the invention. The peptides may be linked by a spacer molecule. The spacer is typically comprised of relatively small, neutral molecules, such as amino acids or amino acids mimetics, which are uncharged under physiological conditions.

A peptide of the invention may be linked to a T helper peptide that is recognized by T helper cells in the majority of the population. This can be accomplished by selecting amino acid sequences that bind to many, most, or all of the HLA class II molecules. An example of such a T helper peptide is tetanus toxoid at positions 830–843 (see, e.g., Panina-Bordignon et al., *Eur. J. Immunol.,* 19:2237–2242 (1989)).

Further, a peptide may be linked to multiple antigenic determinants to enhance immunogenicity. For example, in order to elicit recognition by T cells of multiple HLA types, a synthetic peptide encoding multiple overlapping T cell antigenic determinants (cluster peptides) may be used to enhance immunogenicity (see, e.g., Ahlers et al., *J. Immunol.* 150:5647–5665 (1993). Such cluster peptides contain overlapping, but distinct antigenic determinants. The cluster peptide may be synthesized colinearly with a peptide of the invention. In one embodiment, the cluster peptide may be positioned at the amino terminal end of a peptide of the invention. The cluster peptide may be linked to a peptide of the invention by one or more spacer molecules.

A peptide composition comprising a peptide of the invention linked to a cluster peptide may also be used in conjunction with a cluster peptide linked to a CTL-inducting epitope. Such compositions may be administered via alternate routes or using different adjuvants.

Alternatively multiple peptides encoding CTL and/or HTL epitopes may be used in conjunction with a peptide of the invention.

One embodiment for the use of multiple peptide epitopes known as the multiple antigen peptide system (MAP), utilizes a small peptidyl core matrix with covalently attached, radially branching, multiple synthetic peptides. See, for example, Tam, J. P., *Proc. Natl. Acad. Sci. U.S.A.* 85:5409–5413 (1988). The MAP system is a combination antigen/antigen carrier that is composed of two or more antigenic molecules covalently attached to a dendritic core that is comprised of bifunctional units. The dendritic core of a multiple antigen peptide system can be composed of lysine molecules. For example, a lysine is attached via peptide bonds through each of its amino groups to two additional lysines. This second generation molecule has four free amino groups each of which can be covalently linked to an additional lysine to form a third generation molecule with eight free amino groups. A peptide may be attached to each of these free groups to form an octavalent multiple peptide antigen. Alternatively, the second generation molecule having four free amino groups can be used to form a tetravalent MAPS, i.e., a MAPS having four peptides covalently linked to the core. Many other molecules, including aspartic acid and glutamic acid, can be used to form the dendritic core of a multiple peptide antigen system. The dendritic core, and the entire MAPS may be conveniently synthesized on a solid resin using the classic Merrifield synthesis procedure.

Multiple antigen peptide systems have many advantages as antigen carrier systems. Their exact structure and composition is known; the ratio of antigen to carrier is quite high; and several different antigens, e.g., a B cell epitope such as a peptide of the invention, and a T cell epitope, may be attached to a single dendritic core. When both a B cell epitope and a T cell epitope are present it is preferable that they are linked in tandem on the same functional group of the dendritic core. Alternatively, the T cell epitope and the B cell epitope may be on separate branches of the dendritic core. The T-cell epitope may be a CTL or HTL-inducing antigenic determinant.

*Pseudomonas* toxin conjugation

In another embodiment, the peptides of this invention provides a vaccine comprising a chimeric *Pseudomonas* exotoxin A (PE) protein in which the peptides of this invention are inserted into the Ib domain of the exotoxin. Such chimeric constructs are described in FitzGerald et al., *J. Biol. Chem.,* 273:9951 (1998).

*Pseudomonas* exotoxin A has been shown to act as a carrier-adjuvant for antigens. The protein comprises three prominent globular domains (Ia, II and III) and one small subdomain (Ib). Domain Ia binds to a receptor on most mammalian cell surfaces. Domain II translocates the protein into the cytosol. Domain II has ADP-ribosylating activity which shuts down protein synthesis. The protein can be made non-toxic by, for example, deleting amino acid E553. The protein also can be directed to different cells by exchanging the cell binding domain with ligands for other receptors or antibodies. It comprises a loop formed from a disulfide bond between two amino acids in the domain.

Various genetically modified forms of PE are described, e.g., in U.S. Pat. Nos. 5,602,095; 5,512,658; 5,458,878, and in FitzGerald et al., PCT/US98/14341.

FitzGerald et al. teach a method for replacing amino acid sequences in this loop with sequences from HIV which is applicable to the peptides of this invention. They showed that the non-toxic form of this chimeric protein could elicit HIV-neutralizing antibodies when injected into rabbits. Furthermore, because the chimera gains entry into the cytosol, it may result in the generation of viral peptides and presentation via major histocompatibility complex class I antigens.

Accordingly, this invention provides a recombinant nucleic acid that comprises a nucleotide sequence encoding a chimeric *Pseudomonas* exotoxin A protein wherein a nucleotide sequence encoding a peptide of this invention is inserted into a nucleotide sequence encoding the lb loop of *Pseudomonas* exotoxin A. The peptide of this invention can merely be inserted into the loop or can replace part or all of the loop. In an alternative embodiment, the nucleotide sequence can comprise a nucleotide sequence encoding a ligand for a receptor of choice, wherein the ligand replaces all or part of the Ia domain. In another embodiment, the recombinant nucleic acid is an expression vector comprising an expression control sequence operatively linked to the nucleotide sequence encoding the chimeric immunogen. A host cell can be transfected with the recombinant nucleic acid and the chimeric protein can be expressed thereby.

FitzGerald et al. showed that the chimeric protein can be expressed in a bacterial cell and properly folded so as to have activity. The resulting chimeric immunogens can be used in a vaccine to immunize persons against HIV.

Preparation of peptide-specific antibodies

Monoclonal Antibodies

The monoclonal antibodies of the invention can be made by conventional techniques which are commonly used in hybridoma production (see, e.g. CURRENT PROTOCOLS IN IMMUNOLOGY, Wiley/Greene, NY; and *Antibodies A Laboratory Manual*, Harlow and Lane, Cold Spring Harbor Laboratory Press, 1989). In brief, mice are immunized with the peptides of this invention. B-cells are taken from the spleens of the immunized mice and fused with NS-1 myeloma cells. Polyethylene glycol mixed with dimethyl suffoxide (DMSO) in calcium- and magnesium-free phosphate buffered saline (PBS) can be used as the fusion reagent. The hybridomas generated from the fusion are then transferred to 96 well microtiter plates and grown.

Polyclonal Antibodies

Methods of production of polyclonal antibodies are known to those of skill in the art (e.g., Wiley/Greene and Harlow & Lane, ibid.). In brief, an immunogen, preferably a purified protein, is mixed with an adjuvant and animals are immunized. The animal's immune response to the immunogen preparation is monitored by taking test bleeds and determining the titer of reactivity to the administered protein. When appropriately high titers of antibody to the immunogen are obtained, blood is collected from the animal and antisera are prepared. Further fractionation of the antisera to enrich for antibodies reactive to the protein can be performed if desired.

Single Chain Antibodies

Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker. Huston et al., *Proc. Nat. Acad. Sci. USA,* 85:5879–5883 (1988). While the VH and VL are connected to each as a single polypeptide chain, the VH and VL domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see, e.g., U.S. Pat. Nos. 5,091,513; 5,132,405; and 4,956,778). Particularly preferred antibodies include all those that have been displayed on phage (e.g., scFv, Fv, Fab and disulfide linked Fv (Reiter et al., *Protein Eng,.* 8:1323–1331 (1995)). Antibodies can also include diantibodies and miniantibodies.

Formulation of Immunogenic Compositions

Immunogenic compositions suitable for use as vaccines may be prepared from immunogenic peptides as disclosed herein. The immunogenic composition elicits an immune response which produces antibodies that are opsonizing or antiviral. Should the vaccinated subject be challenged by HIV-1, the antibodies bind to the virus and thereby inactivate it.

Vaccines containing peptides are generally well known in the art, as exemplified by U.S. Pat. Nos. 4,601,903; 4,599,231; 4,599,230; and 4,596,792. Vaccines may be prepared as injectables, as liquid solutions or emulsions. The peptides may be mixed with pharmaceutically-acceptable excipients which are compatible with the peptides. Excipients may include water, saline, dextrose, glycerol, ethanol, and combinations thereof. The vaccine may further contain auxiliary substances such as wetting or emulsifying agents, pH buffering agents, or adjuvants to enhance the effectiveness of the vaccines.

More specifically, the immunogens of this invention may be combined or mixed with various solutions and other compounds as is known in the art. For example, an immunogen may be administered in water, saline or buffered vehicles with or without various adjuvants or immunodiluting agents. Examples of such adjuvants or agents include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, *Corynebacterium parvum* (*Propionobacterium acnes*), *Bordetella pertussis*, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.). Other suitable adjuvants are Amphigen (oil-in-water), Alhydrogel (aluminum hydroxide), or a mixture of Amphigen and Alhydrogel. Only aluminum is approved for human use.

Conveniently, the vaccines are formulated to contain a final concentration of immunogen in the range of from 0.2 to 200 μg/ml, preferably 5 to 50 μg/ml, most preferably 15 μg/ml. After formulation, the vaccine may be incorporated into a sterile container which is then sealed and stored at a low temperature, for example 4° C., or it may be freeze-dried. Lyophilization permits long-term storage in a stabilized form.

For suppositories, binders and carriers may include, for example, polyalkalene glycols or triglycerides. Oral formulations may include normally employed incipients such as, for example, pharmaceutical grades of saccharine, cellulose and magnesium carbonate. These compositions take the form of solutions, suspensions, tablets, pills, capsules, sustained release formulations or powders and contain 10–95% of the peptides.

The peptides of this invention can be formulated for administration via the nasal passages. Formulations suitable for nasal administration, wherein the carrier is a solid, include a coarse powder having a particle size, for example, in the range of about 10 to about 500 microns, which is administered in the manner in which snuff is taken, ie., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active ingredient. For further discussions of nasal administration of AIDS-related vaccines, references are made to the following U.S. Pat. Nos.: 5,846,978; 5,663,169; 5,578,597; 5,502,060; 5,476,874; 5,413,999; 5,308,854; 5,192,668; and 5,187,074.

Administration

The vaccines may be administered by any conventional methods including oral administration and parenteral (e.g., subcutaneous or intramuscular) injection. The treatment may consist of a single dose of vaccine or a plurality of doses over a period of time. The immunogen of the invention can be combined with appropriate doses of compounds including other epitopes of the target bacteria. Also, the immunogen could be a component of a recombinant vaccine which could be adaptable for oral administration.

The proportion of immunogen and adjuvant can be varied over a broad range so long as both are present in effective amounts. For example, aluminum hydroxide can be present in an amount of about 0.5% of the vaccine mixture ($Al_2O_3$ basis). On a per-dose basis, the amount of the immunogen can range from about 5 μg to about 100 μg protein per patient of about 70 kg. A preferable range is from about 20 μg to about 40 μg per dose. A suitable dose size is about 0.5 ml. Accordingly, a dose for intramuscular injection, for example, would comprise 0.5 ml containing 20 μg of immunogen in admixture with 0.5% aluminum hydroxide.

Vaccines of the invention may be combined with other vaccines for other diseases to produce multivalent vaccines. A pharmaceutically effective amount of the immunogen can be employed with a pharmaceutically acceptable carrier such as a protein or diluent useful for the vaccination of mammals, particularly humans. Other vaccines may be prepared according to methods well-known to those skilled in the art.

The therapeutic application of AIDS vaccines can be done by way of nasal administration. Various ways of such administration are known in the art. The pharmaceutical formulation for nasal administration may be prepared as solutions in saline, employing benzyl alcohol or other suitable preservatives, absorption promoters to enhance bioavailability, fluorocarbons, and/or other solubilizing or dispersing agents known in the art. The unit dosage for nasal administration can be from 1 to 3000 mg, preferably 70 to 1000 mg, and most preferably, 1 to 10 mg of active ingredient per unit dosage form.

Alternatively, other modes of administration including suppositories and oral formulations may be desirable.

The peptides of the present invention may also be administered in conjunction with immune stimulating complexes (ISCOMS) ISCOMS are negatively charged cage-like structure of 30–40 nm in size formed spontaneously on mixing cholesterol and Quil A (saponin). Protective immunity has been generated in a variety of experimental models of infection including toxoplasmosis and Epstein-Barr virus-induced tumors using ISCOMS as the delivery vehicle for antigens (see, e.g., Mowat and Donachie, *Immunol. Today,* 23:383–385 (1991)). Immunogenic compositions using ISCOMS are comprised of the peptides of the invention encapsulated into ISCOMS for delivery.

Immunotherapy regimens which produce maximal immune responses following the administration of the fewest number of doses, ideally only one dose, are highly desirable. This result can be approached through entrapment of immunogen in microparticles. For example, the absorbable suture material poly(lactide-co-glycolide) co-polymer can be fashioned into microparticles containing immunogen (see, e.g., Eldridge et al., *Molec. Immunol.,* 28:287–294 (1991); Moore et al., *Vaccine* 13:1741–1749 (1995); and Men et al., *Vaccine,* 13:683–689 (1995)). Following oral or parenteral administration, microparticle hydrolysis in vivo produces the non-toxic byproducts, lactic and glycolic acids, and releases immunogen largely unaltered by the entrapment process. Microparticle formulations can also provide primary and subsequent booster immunizations in a single administration by mixing immunogen entrapped microparticles with different release rates. Single dose formulations capable of releasing antigen ranging from less than one week to greater than six months can be readily achieved.

The peptides of the invention may also be administered via liposomes, which serve to target the peptides to a particular tissue, such as lymphoid tissue, or targeted selectively to infected cells, as well as increase the half-life of the peptide composition. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.,* 9:467 (1980), and U.S. Pat. Nos. 4,235,871; 4,501,728; 4,837,028; and 5,019,369.

Nucleic acid vaccines

Nucleic acids (typically DNA) encoding the polypeptides of the invention are administered to patients to elicit an immune response against the polypeptides which they encode. DNA administered for this purpose is referred to as a "DNA vaccine." Methods of making and administering DNA as vaccines are known, and described, e.g., in Wolff et. al., *Science,* 247:1465–1468 (1990).

In general, the dose of a naked nucleic acid composition such as a DNA vaccine or gene therapy vector is from about 1 μg to 100 μg for a typical 70 kilogram patient. The immunogenic composition can be either a nucleic acid encoding the target protein (e.g., a DNA vaccine) or a virus vector which produces the antigenic protein. Subcutaneous or intramuscular doses for naked nucleic acid (typically DNA encoding a fusion protein) will range from 0.1 μg to 500 μg for a 70 kg patient in generally good health. Subcutaneous or intramuscular doses for viral vectors comprising the fusion proteins of the invention will range from $1\times10^5$ pfu to $1\times10^9$ for a 70 kg patient in generally good health.

Passive immunization

Passive immunotherapeutic methods are applicable to persons exhibiting symptoms of HIV-induced disease, including AIDS or related conditions believed to be caused by HIV infection, and humans at risk of HIV infection. Patients at risk of infection by HIV include babies of HIV-infected pregnant mothers, recipients of transfusions known to contain HIV, users of HIV contaminated needles, individuals who have participated in high risk sexual activities with known HIV-infected individuals, and the like risk situations.

HIV has been disclosed as treatable using passive immunization. See for example Jackson et al., *Lancet*, September 17:647–652, (1988); Karpas et al., *Proc. Natl. Acad. Sci, USA* 87:7613–7616 (1990), Eichberg et al., *AIDS Res. Hum. Retroviruses* 8:1515 (1992) and U.S. Pat. No. 5,830,476. Passive immunization can be accomplished with polyclonal antibodies, monoclonal antibodies, or antibody fragments.

In one embodiment, the passive immunization method comprises administering a composition comprising more than one species of human monoclonal antibody of this invention, preferably directed to non-competing epitopes or directed to distinct serotypes or strains of HIV, as to afford increased effectiveness of the passive immunotherapy.

A therapeutically (immunotherapeutically) effective amount of a humanized or human antibody is a predetermined amount calculated to achieve the desired effect, i.e., to neutralize the HIV present in the sample or in the patient, and thereby decrease the amount of detectable HIV in the sample or patient. In the case of in vivo therapies of persons already infected, an effective amount can be measured by improvements in one or more symptoms associated with HTV-induced disease occurring in the patient, or by serological decreases in HIV antigens.

Thus, the relevant dosage ranges for the administration of the monoclonal or other antibodies of the invention are those large enough to produce the desired effect in which the symptoms of the HIV disease are ameliorated or the likelihood of infection decreased. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication.

A therapeutically effective amount of an antibody of this invention is typically an amount of antibody such that when administered in a physiologically tolerable composition is sufficient to achieve a plasma concentration of from about 0.1 $\mu$g/ml to about 100 $\mu$g/ml, preferably from about 1 $\mu$g/ml to about 5 $\mu$g/ml, and usually about 5 $\mu$g/ml. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

The antibodies of the invention can be administered parenterally by injection or by gradual infusion over time. Although the HIV infection is typically systemic and therefore most often treated by intravenous administration of therapeutic compositions, other tissues and delivery means are contemplated where there is a likelihood that the tissue targeted contains infectious HIV. Thus, antibodies of the invention can be administered intravenously, intraperitoneally, intramuscularly, subcutaneously, intracavity, transdermally, and can be delivered by peristaltic means.

The therapeutic compositions containing antibodies of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; ie., carrier, or vehicle.

Diagonostic uses in immunoassays and other uses

Immunoassays

The peptides of this invention or or antibodies specific to the peptides themselves can be used to detect the presence of HIV in serum or in any biological sample. The assays will find use in both medical and research settings.

Normally, the peptides are in the range of about 9 residues and up to about 40 residues. The preferred range is 9 to 25 residues. There may be circumstances where a mixture of peptides from conserved regions and/or from the non-conserved regions are used to provide cross-isolate protection and/or diagnosis. In this instance, the mixture of peptide immunogens is commonly referred to as a "cocktail" preparation for use as an immunogenic composition or a diagnostic reagent. The peptides of this invention can be used in such a peptide.

The peptides of the present invention are useful as antigens in immunoassays which include but are not limited to enzyme-linked immunosorbent assays (ELISA), RIAs, and other non-enzyme linked antibody binding assays, or procedures known in the art for the detection of anti-HIV antibodies. For a review of immunological and immunoassay procedures in general, see *Basic and Clinical Immunology* 7th Edition (D. Stites and A. Terr, eds.) 1991. Moreover, the immunoassays of the present invention can be performed in any of several configurations, which are reviewed extensively in *Enzyme Immunoassay*, E. T. Maggio, ed., CRC Press, Boca Raton, Fla. (1980); "Practice and Theory of Enzyme Immunoassays," Tijssen; and in *Antibodies A Laboratory Manual*, Harlow and Lane, Cold Spring Harbor Laboratory Press, 1989.

In ELISA assays, for example, the peptides are immobilized onto a selected surface, for example a surface capable of binding peptides, such as the wells of a polystyrene microtitre plate. After washing to remove incompletely adsorbed peptides, a non-specific protein, such as a solution of bovine serum albumin (BSA) or casein, that is known to be antigenically neutral with regard to the test sample may be bound to the selected surface. This allows for blocking of non-specific adsorption sites on the immobilizing surface and thus decreases the background caused by non-specific bindings of antisera onto the surface.

The immobilizing surface is then contacted with a sample, such as clinical or biological materials to be tested, in a manner conducive to immune complex (antigen/antibody) formation. This may include diluting the sample with diluents such as solutions of BSA, bovine gamma globulin (BGG) and/or phosphate buffered saline (PBS)/Tween. The sample is then allowed to incubate for from about 2 to 4 hours, at temperatures such as of the order of about 25° to 37° C. Following incubation, the sample-contacted surface is washed to remove non-immunocomplexed material. The washing procedure may include washing with a solution such as PBS/Tween, or a borate buffer.

Following formation of specific immunocomplexes between the test sample and the bound peptides, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity, such as an enzymatic activity that will generate, for example, a color development upon incubating with an appropriate chromogenic substrate. Quantification may then be achieved by measuring the degree of color generation using, for example, a visible spectra spectrophotometer.

Other uses

Molecules which bind to the conserved sequences on which the invention is based, particularly binding proteins, antibodies, antibody-related molecules and structural analogs thereof, are also of possible use as agents in the treatment and diagnosis of AIDS and related conditions.

For targeted delivery of toxins or other agents, e.g., by use of immunotoxins comprising conjugates of antibody to the relevant peptides and a cytotoxic moiety, for binding directly or indirectly to a target conserved sequence of, for example, or gp120 or gp41.

For targeted delivery of highly immunogenic materials to the surface of HIV-infected cells, leading to possible ablation of such cells by either the humoral or cellular immune system of the host.

For detection of HIV, e.g., using a variety of immunoassay techniques.

In yet a further diagnostic embodiment, the peptides of the present invention (individually, or as mixtures including cocktail preparations) are useful for the generation of HIV-1 antigen-specific antibodies (including monoclonal antibodies) that can be used to detect HIV-1 or specific antigens thereof, or to neutralize HIV-1 in samples including biological samples.

In an alternative diagnostic embodiment, the peptides of the present invention can be used to specifically stimulate HIV-specific B-cells in biological samples from, for example, HIV-infected individuals.

A further diagnostic embodiment includes the use of the peptides to determine prognosis for Long Term Non-Progressor patients towards AIDS.

The above disclosure generally describes the present invention. A more complete understanding can be obtained by reference to the following specific Examples. These Examples are described solely for purposes of illustration and are not intended to limit the scope of the invention. All references are herein incorporated by reference.

EXAMPLES

The following examples are provided by way of illustration only and not by way of limitation. Those of skill will readily recognize a variety of noncritical parameters which could be changed or modified to yield essentially similar results.

Example 1

Identification of HIV specific phagotopes a. Affinity selection of HIV-1 mimotopes In order to select for B cell epitopes specifically recognized by serum antibodies of HIV-1-infected subjects, random phage libraries (RPLs) displayed on phages were screened with HIV-1 positive sera from long-term non-progressor (LTNP) subjects. This population was chosen because LTNP subjects show higher titers of neutralizing antibodies than sera from AIDS patients (Montefiori et al., *J. Infect. Dis.* 173:60 (1996)). In order to maximize the detection of HIV-specific peptides, phagotopes were first selected by immuno-affinity purification with the IgG of one HIV-1 positive LTNP individual, and then subjected to immunoscreening by using a second HIV-1 positive LTNP serum.

More particularly, human sera were collected from HIV-1 positive or HIV-1 negative control subjects. Criteria for definition of long term non-progression of AIDS were as previously described (Pantaleo et al., *N. Engl. J. Med.* 332:209 (1995)). Two peptide libraries composed of random nonamers displayed on the N terminus of pVIII major coat protein of filamentous phages either unconstrained (pVIII9aa) (Felici et al., *J. Mol. Biol.* 222:301 (1991)), or flanked by two cysteines (pVIII9aa-cys) (Luzzago et al., *Gene* 128:5 (1993)) were screened as described (Prezzi et al.,. *J. Immunol.* 156:4504 (1996)).

In the immunoaffinity selection, serum IgG was linked to magnetic microbeads (tosyl-activated Dynabeads M450; Dynal, Lake Success, N.Y.) previously coated with an anti-human (Fc-specific) polyclonal antibody (goat anti human IgG Fe-specific; Sigma, SL Louis, Mo.) at 200 μg/ml of beads suspension. $2\times10^{11}$ transducing units (TU) of phage particles were applied to IgG-coated beads and incubated for 16 h at 4° C. After extensive washing, bound phages were eluted with 0.1 M HCl/glycine buffer pH 2.2 and neutralized.

b. Immunoscreening

The secondary immunoscreening was performed as follows: TG-1 cells were infected with eluted phages at a multiplicity of infection (MOI) of $1\times10^{-3}$ and plated at a density of $1\times10^{4}$ TU/plate. The following day, bacterial colonies were collected, amplified and superinfected with M13K07 at an MOI of 50. Two thousand colonies were replated on a lawn of TG-1 cells in the presence of 35 μg/ml of isopropyl-1-thio-β-D-galactoside (IPTG). Plates were layered with nitrocellulose filters for 16 h at 37° C. Filters were incubated with serum at a 1:50 dilution in immunoscreening buffer (5% non-fat dry milk, 0.1% Nonidet p40, $3\times10^{11}$ wild-type phages, $5\times10^{9}$ M13K07 UV-killed phages/ml, 10 μl of TGI bacterial extract) for 16 h, at 4° C. Positive colonies were detected by an anti-human (Fc-specific) alkaline phosphatase-conjugated antibody (Sigma).

To validate that the bound phagotopes carry HIV-specific epitopes, positive colonies were tested by ELISA for reactivity with sera from multiple HIV-infected individuals and counter-screened with an equivalent number of sera from HIV-negative subjects. For the EJISA analysis, microtiter plates were coated with anti M13 antibody (Pharmacia, Piscataway, N.J.) at 10 μg/ml overnight at 4° C. in coating buffer. Fifty μl of cleared phage supernatant with an equal volume of blocking buffer were incubated for 1 h at 37° C. Plates were washed extensively and supplemented with human serum at 1:100 dilution followed by an overnight incubation at 4° C. After washing, wells were coated with an anti-human (Fc-specific) alkaline phosphatase-conjugated antibody. Plates were washed and developed. Results were expressed as the difference between $OD_{405\ nm}$ and $OD_{620\ nm}$ by an ELISA reader.

There were two selections. In selection 1, LTNP sera 6090 and 3976 were utilized for immunoaffinity and immunoscreening steps, respectively. Similarly, selection 2 was performed by using LTNP sera 3872 and 8075. Selection 1, performed on a cysteine constrained pVIII9aa-cys library (Luzzago et al, *Gene* 128:5 (1993)), resulted in the identification of five HIV-specific clones; selection 2, conducted on an unconstrained pVIII9aa library (Felici et al., *J. Mol. Biol.* 222:301 (1991)) led to isolation of five additional phagotopes (FIG. 1*a*).

All the selected clones were found to react with 22 LTNP sera and 25 AIDS sera with a recognition frequency (f) ranging from 23 to 64%; all clones tested negative by ELISA with 50 HIV-negative sera. It was highly unlikely that the frequency distribution of each phagotope between HIV positive and negative sera could have occurred by chance (p<0.001). Accordingly, the clones were considered HIV-1-specific phagotopes. Each serum manifested a distinct pattern of reactivity with the pool of phagotopes (FIG. 1*a*). Some sera, such as 8873 and 1276, recognized most phagotopes indicating a broad antibody specificity, whereas sera 2214, 5223, and 8075 reacted with only one phagotope.

Figure 1B:
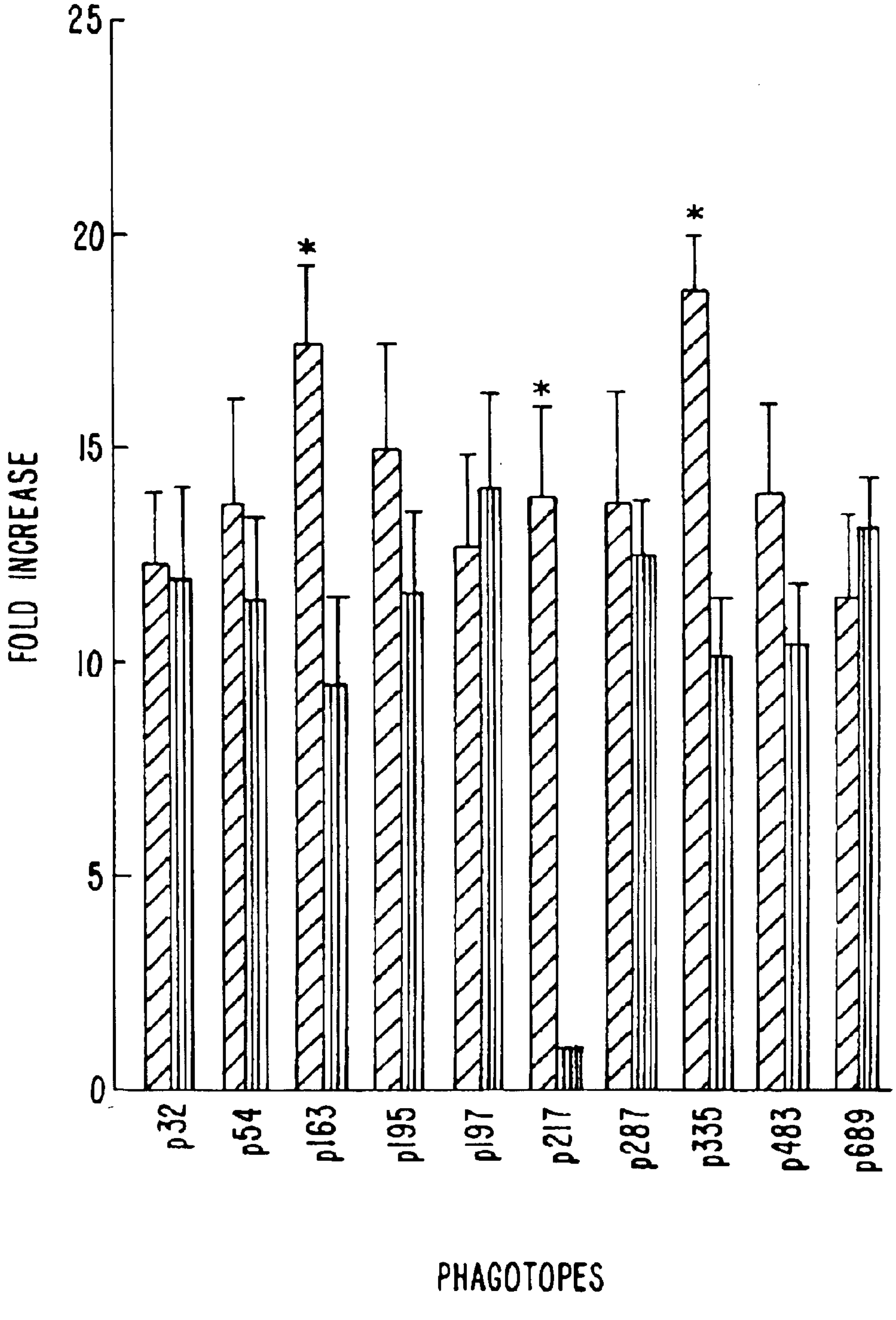

Clone p217 was restricted in its reactivity to a subset of LTNP sera (f: 23); however, it was completely unreactive with a pool of AIDS sera (FIG. 1*a*). This suggests that p217-specific antibodies may exert a protective role in disease progression. Analysis of the reactivities of sera for each phagotope showed that antibody titers to p163, p217 and p335 were significantly higher in sera from LTNPs than from AIDS patients ($p<0.05$, FIG. 1*b*). Again, these results suggest that antibody responses to these epitopes might afford a degree of protection against disease progression.

Example 2

Characterization of HTV-1 mimotopes

Figure 2:
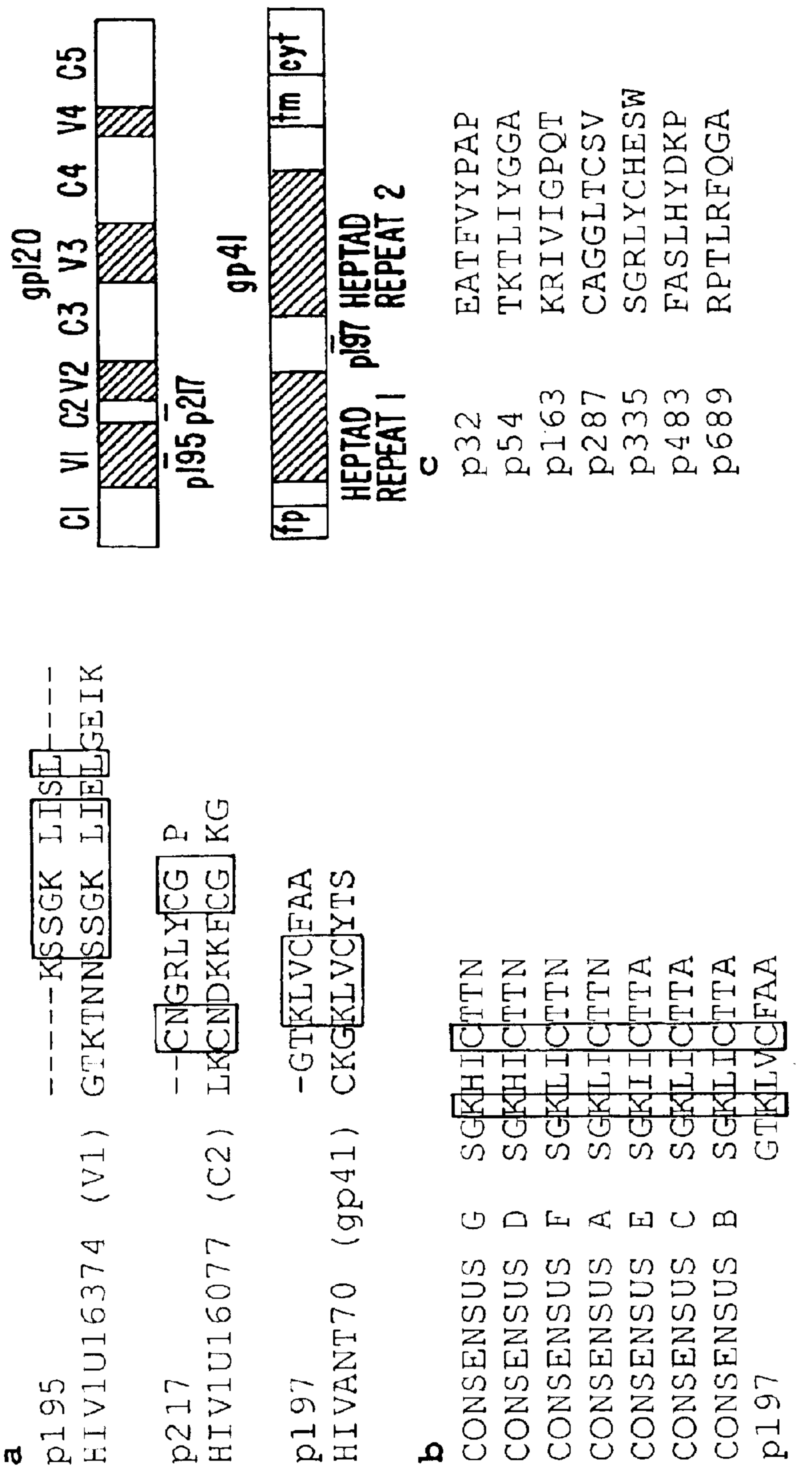
FIG. 2. Amino acid sequences of the HIV-specific phagotopes. The amino acid sequences of peptides displayed on the HIV-specific phagotopes are shown as single letter codes. a, Homology between the amino acid sequences of p195, p217 and p197 and discrete regions of HIV gp160. Gray boxes indicate identity; similarity among amino acid residues is indicated as gray shading. b, consensus homology of p197 with a gp41 domain conserved between HIV-1 subtypes A through G. c, Amino acid sequences of epitopes with no obvious sequence homology with HIV protein domains.

The amino acid sequences of the phage-displayed peptides are shown in FIG. 2. A BLAST analysis revealed that the p195 epitope shares sequence homology with the gp120 V1 region (residues 112–120) of HIV1-U116374, a primary isolate from an acute seroconverter (Zhu et al., *J. Virol.* 69:1324 (1995)); the p217 sequence matched with the gp120 C2 region (residues 198–205) of HIV1-U116077, a primary isolate from an AIDS patient (Shapshak et al., *Adv. Exp. Med. Biol.,* 373:225 (1995)) (FIG. 2*a*).

Residues within these regions have been predicted to be immunologically accessible by selected mAbs and by X ray crystal structure (Kwong et al., *Nature* 393:648 (1998); Wyatt et al., *Nature* 393:705 (1998)). Moreover, the p197 epitope mapped to a region of gp41 (residues 602–605) of the HIVANT170 primary isolate (Vanden et al., *J. Virol.* 68:1586 (1994)). This region is conserved among primary isolates of HIV subtypes A through G and defines a disulfide-bonded structure important for the association of gp120 and gp41 (Cotropia et al., *J. Acquir. Immune Defic. Syndr. Hum. Retrovirol.* 12:221(1996)). Moreover, this domain is proximal to an exposed region of gp41 containing the linear epitope ELDKWA recognized by 2F5, a monoclonal antibody capable of neutralizing a majority of a panel of typical primary isolates identified in the United States (D'Souza et al., *J. Infect. Dis.* 175:1056(1997)) (FIG. 2*a,b*). Thus, the peptides expressed on p195, p217, and p197 are antigenic mimics of epitopes expressed in primary HIV isolates from subjects at different stages of disease. No sequence homology with HIV proteins was found in the remaining clones, suggesting that they may represent immunological mimics of conformational HIV-1 epitopes (FIG. 2*c*).

Example 3

Immunoaffinity of antibodies specific to the peptides

The antibody reactivities shown in FIG. 1*a* indicate that the phage-displayed peptides behave as antigenic mimics of viral determinants generated in the course of HIV infection. Therefore, it is possible to immunoaffinity purify antibodies specific for each phagotope from sera of HIV-infected individuals by using single phagotopes as ligands. To this end, p195, p197, p217, p287 and p335 were utilized to purify the phagotope-specific antibodies from LTNP serum 6090.

Affinity purification of phagotope specific human antibodies was accomplished using 60 mm diameter dishes coated with $5\times10^{11}$ CsCl-purified phages overnight at 4° C. After washing and blocking, human serum (1:100 dilution) was added and incubated for 16 h at 4° C. After extensive washing, bound antibodies were eluted with glycine-HCl buffer pH 2.2. Antibody concentration was determined by an in-house ELISA with a low detection level of 1–2 ng/ml.

Figure 3:
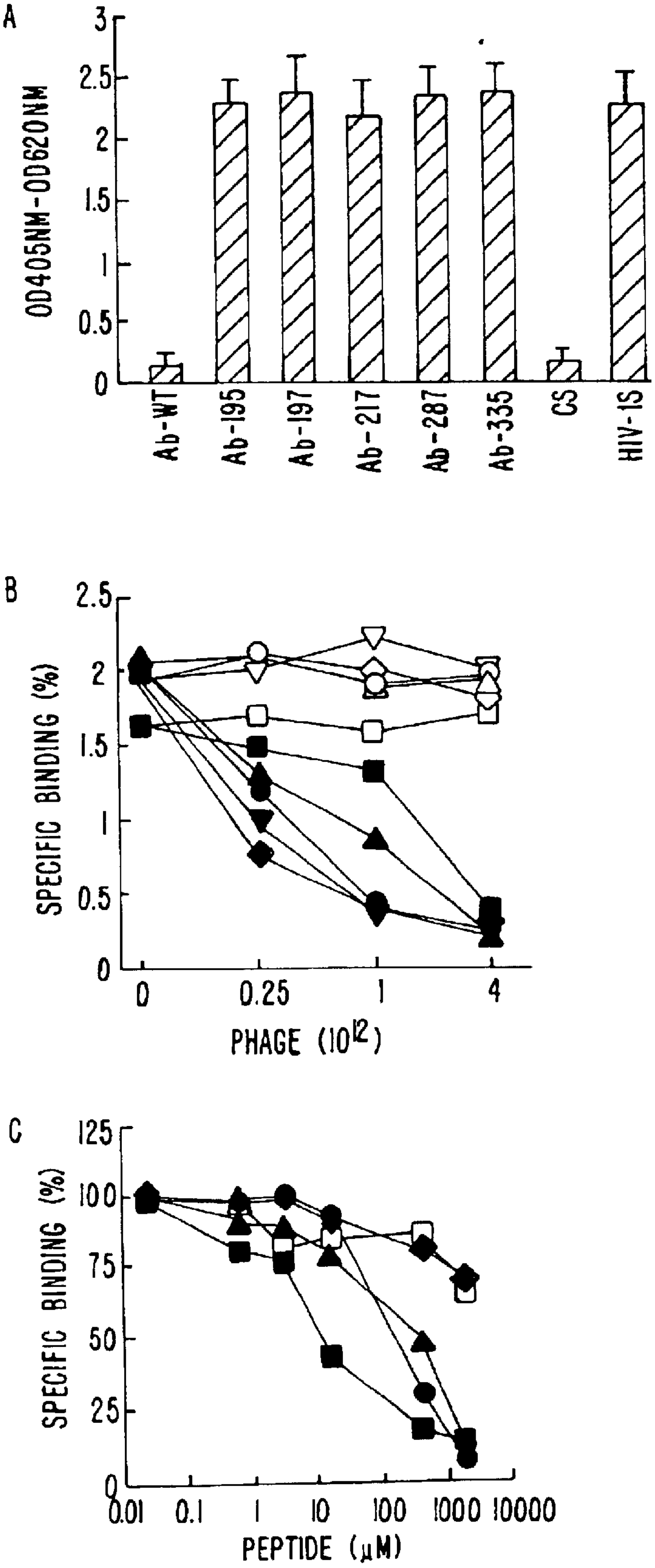
FIG. 3. Phagotope-specific antibodies bind to HIV-1. a, ELISA reactivities of immunoaffinity purified antibodies with HIV-1. Antibodies were immunoaffinity purified from LTNP serum 6090 using single phagotopes as ligands and tested for ELISA reactivity against HIV-1 virions by using a standard ELISA kit (Organon). Purified antibodies were tested at 5–10 ng/ml; HIV-negative (CS) and serum 6090 (HIV-1S) were tested at 1:100 dilution. Data are expressed as mean±SEM of four independent determinations. b, The binding of phagotope-specific antibodies to HIV-1 is specifically displaced by the related phagotopes. ELISA reactivities of single immunopurified antibodies to HIV-I were tested in the presence of the indicated concentrations of p195 (■), p197 (♦), p217 (●), p287 (▲), p335(▼). The binding of each antibody to HIV was also tested in presence of increasing concentrations of wild-type phages (open symbols). c, Displacement of HIV-1 binding by peptides corresponding to the phage-displayed epitopes shown in FIG. 2*a,c*. ELISA reactivities of single immunoaffinity purified antibodies with the related phagotopes were tested in the presence of increasing concentrations of peptides 195 (■), 197 (▲), 217 (♦), 287 (ρ), 335 (●). d, HIV-1 immunoblotting with phagotope-specific human antibodies. Immunoffinity purified antibodies were tested at 60 ng/ml for binding to HIV-1 proteins in Western blot by a diagnostic kit (Cambridge Biotech.); 6090 LTNP serum was tested at 1:1000 dilution.
Figure 3:
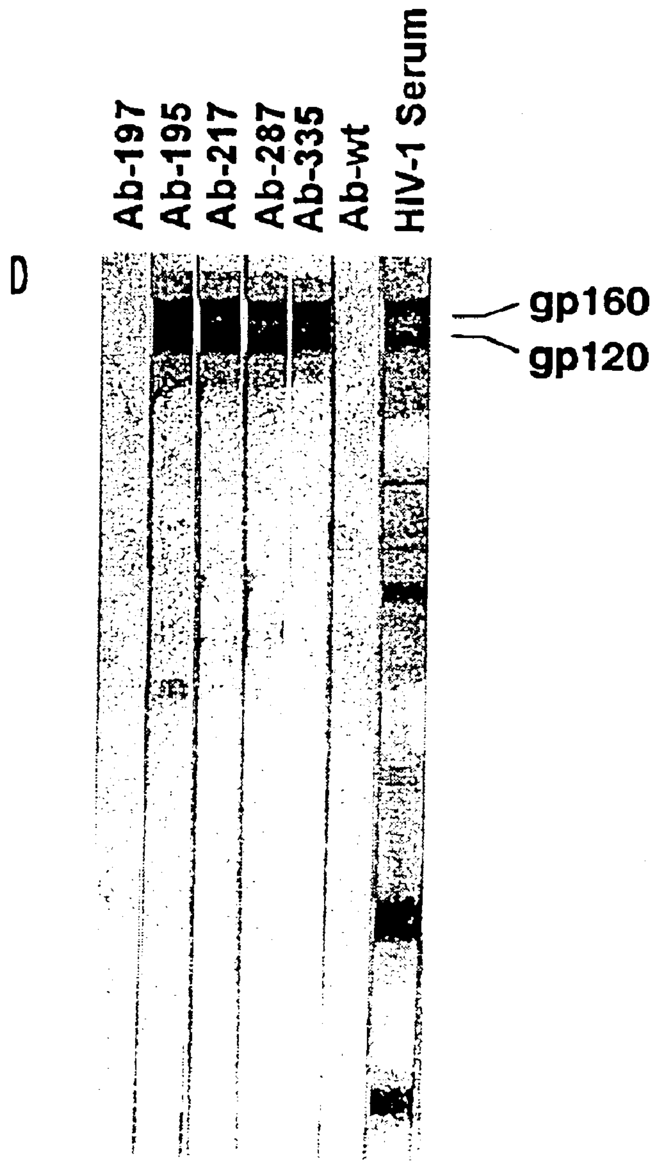

The phagotope specific antibodies, purified from serum to IgG concentrations of 5–10 ng/ml, recognized HIV-1 proteins by ELISA (FIG. 3*a*); this reactivity was specifically displaced by the related phagotopes, but not by wild-type or unrelated phages (FIG. 3*b* and data not shown). Moreover, peptides corresponding to the epitopes displayed on phages p195, p197, and p335 effectively displaced the binding of Abs to HIV-1, indicating that these peptides acquire in solution a conformation similar to the one expressed by both the phage-displayed peptides and the HIV epitopes (FIG. 3*c*). Only a partial competition was observed in the case of peptide 217 and 287, indicating that expression of these peptides on the surface of the phages is essential to acquire a conformation mimicking HIV epitopes (FIG. 3*c*), as previously suggested (Meola et al., *J. Immunol.,* 154:3162 (1995)).

When the phagotope-specific antibodies were tested in immunoblotting, a distinctive reactivity was found. Ab-195 and Ab-217 recognized gp160 and gp120, consistent with the mapping of these epitopes at envelope regions. In addition, Ab-287 and Ab-335 also detected HIV-gp160 and gp120, indicating that they recognized envelope-specific epitopes (FIG. 3*d*). No bands were detected by p197-specific antibodies, indicating an intrinsic inability of these antibodies to bind to the cognate epitope under denaturing conditions (FIG. 3*d*).

Example 4

HIV-1 mimotopes react specifically with sera of SHIV-infected monkeys

Simian HIV [SHIV] recombinant viruses expressing HIV env on the backbone of SIV isolates are a useful model of HIV-1 infection in primates (Shibata el al, *J. Virol.* 71:8141 (1997)). SHIV-infected monkeys raise high titers of neutralizing Abs that correlate with long-lasting protection from subsequent challenge with pathogenic SHIV (Igarashi et al., *J. Gen. Virol.* 78:985 (1997)) or SIV-mac239 (Miller er al, *J. Virol.* 71:1911 (1997)). Since the HIV-specific phagotopes are immunogenic mimics of HIV-1 env proteins (FIG. 1-3), they should be recognized by antibodies of SHIV-infected animals.

Figure 4:
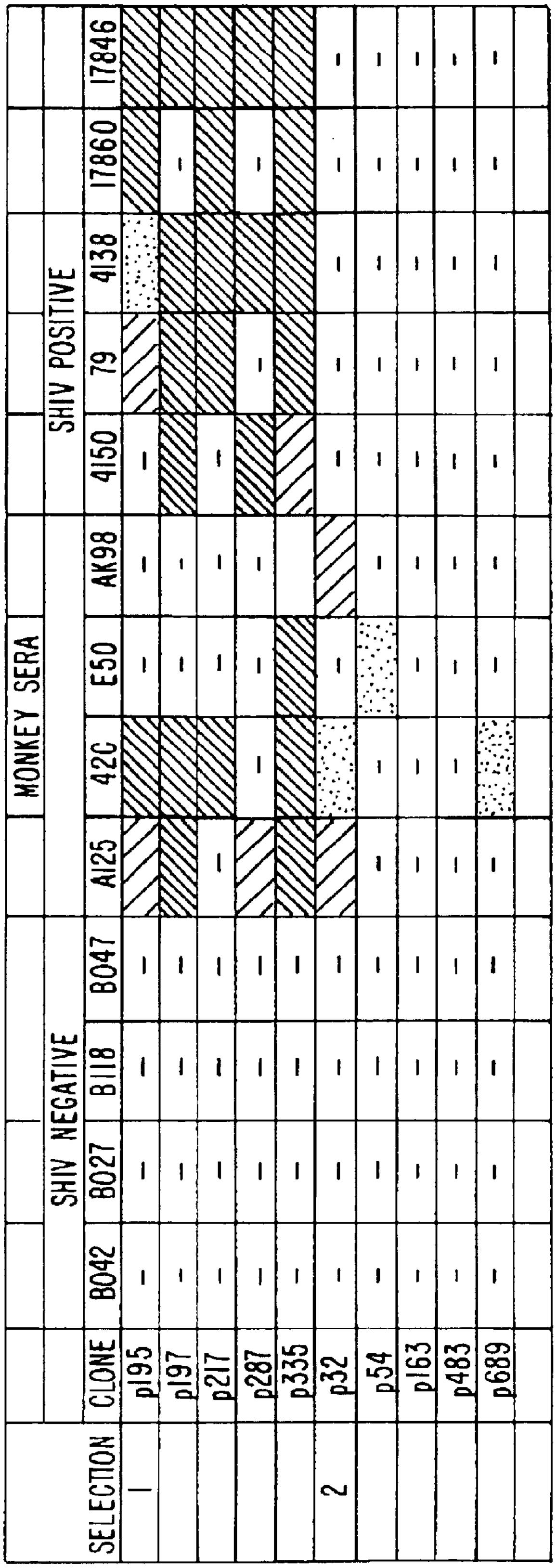
FIG. 4. ELISA reactivities of monkey sera with HIV-specific phagotopes. Sera of naive monkeys (SHIV Negative) and SHIV-infected animals were tested for binding to HIV-1 phagotopes. Results are expressed as fold increase of $OD_{405\ nm}$ values of tested phagotope over the $OD_{405\ nm}$ values of wild-type-phage. Cutoff values were set as detailed in the legend to FIG. 1*a*. All the pre-infection sera of SHIV-positive animals tested negative by ELISA (not shown). A125, 42C, E50 and AK98 are Rhesus macaques; 4138, 4150 and 79 are cynomologous macaques; these animals were infected with $SHIV_{MD1}$ (Shibata et al., *J. Infect. Dis.* 176:362 (1997)). 17860 and 17846 are pigtail macaques infected with $SHIV_{MD14YE}$ (Shibata et al., *J. Infect. Dis.* 176:362 (1997)).

In order to test this hypothesis, sera of nine SHIV-infected monkeys and of four uninfected control animals were tested for ELISA reactivity with the pool of HIV mimotopes. As in the case of HIV-1 infected subjects (FIG. 1*a*), sera of SHIV-infected monkeys recognized the HIV-1 phagotopes with variable frequencies (FIG. 4). As previously noted, phagotopes p32, p54, and p689 did not match any HIV sequences in the database (FIG. 2*c*). The fact that certain SHIV sera recognized these phagotopes suggests that they are conformational mimics of discrete regions of gp 160, Nef or Tat, since these are the only HIV-specific sequences within SHIV.

Phagotope p 163 and p483, which were consistently recognized by LTNP and AIDS sera (FIG. 1*a*), did not react with SHIV sera, suggesting that they are antigenic mimics of HIV-1 epitopes encoded for gag or pol genes. Sera from uninfected monkeys tested negative in ELISA (FIG. 4). These results indicate that macaques are genetically similar to humans in antigen processing and presentation, since their antibodies efficiently recognized human B-cell epitopes; in this regard, the selected phagotopes should induce HIV-specific antibodies, and could be exploited to immunize monkeys before SHIV challenge.

Example 5

Production of neutralizing antibodies

HIV-1 mimotopes induce neutralizing antibodies in mice

The HIV-1-binding antibodies of this invention exert neutralizing activity in vitro if directed to accessible epitopes of infectious virions. As antigenic mimics of HIV-1 epitopes, HIV-1 phagotopes have a conformation that fits in the antigen-binding site of the related serum antibodies, and would be expected to elicit antibodies in vivo with specificities similar to the original serum IgG utilized to select them. To establish the neutralizing effects of the peptides of this invention, HIV-1 phagotopes p195, p197, p217, p287 and p335 were used to immunize BALB/c or C57B/6 mice.

Phage were CsCl purified and used at a concentration of $6\times10^{12}$ particles/ml in 0.9% NaCl with an equal volume of CFA or IFA. Four to five-week-old female BALB/c and C57B1 mice were immunized by i.p. injection of 200 $\mu$l of antigen emulsion at weeks 0, 3, 6, 9, 12 and bled on day 0 and day 7–10 after each additional injection. Serum IgG was purified from mouse sera with T-Gel Adsorbent (Pierce, Rockford, Ill.).

All mice developed comparable titers of Abs against wild-type phages, and a strong antibody response to the original phagotopes used as immunogens (not shown). To determine the neutralizing effects of the antibodies, neutralization of $HIV_{IIIB}$ and NL4-3 molecular clones was measured in a MT-2 assay (Montefiori et al. *J. Clin., Microbiol.* 26:231 (1988)). Briefly, cell free virus (500 $TCID_{50}$/ml) and serial dilutions of mouse IgG were incubated in triplicate at 37° C. for 1 h before the addition of MT-2 cells ($5\times10^4$/well). At 6–8 days post infection, neutralization was quantified by staining viable cells with neutral red followed by colorimetric determination of uptake at 540 nm. In the case of AD8, neutralization assay was performed on PHA-activated PBMC as described (Montefiori et al., *J. Virol.* 72:1886 (1998)).

Figure 5:
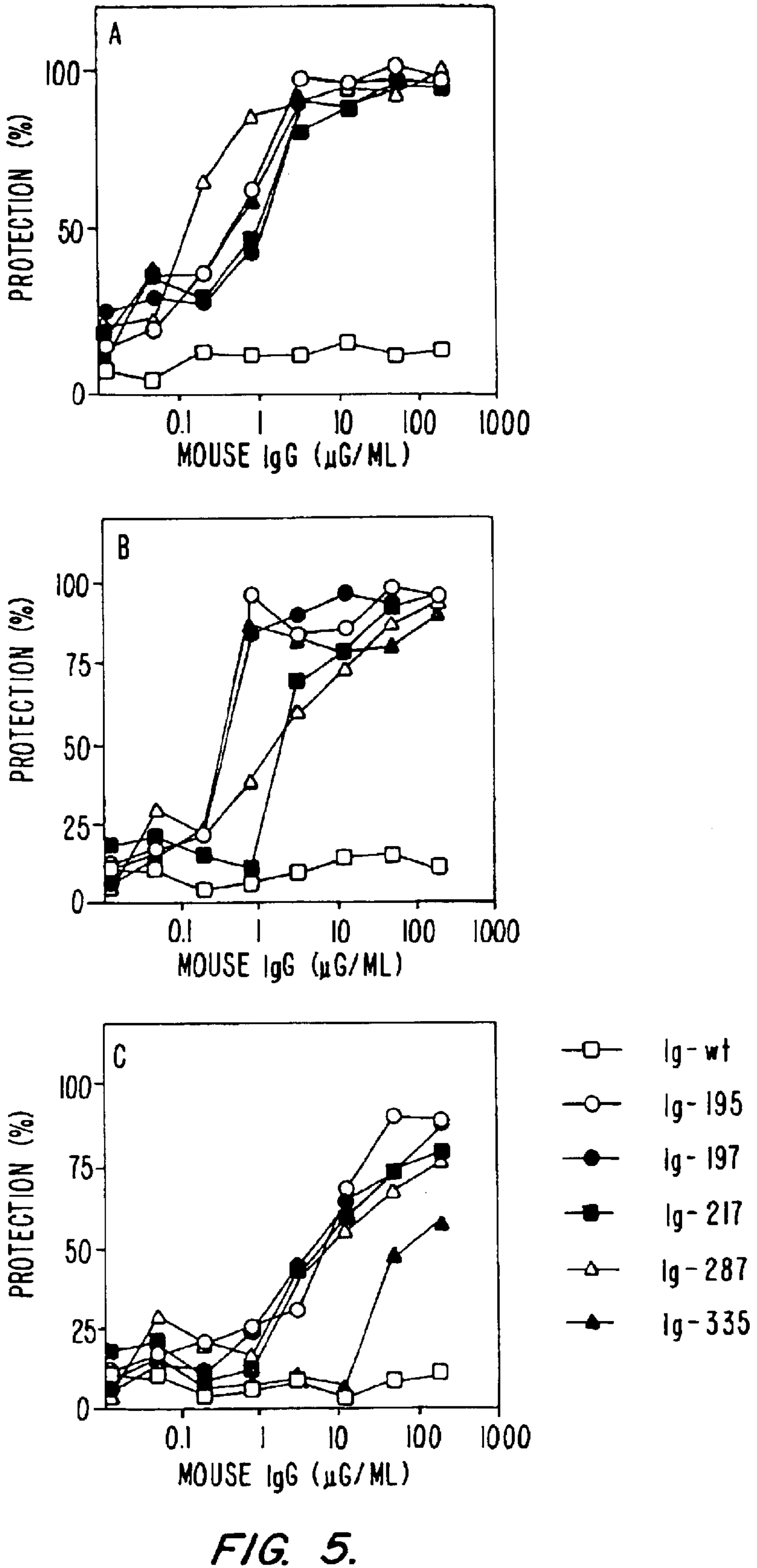
FIG. 5. Assays of the neutralization of HIV-1 by phagotope-specific antibodies. C57B16 mice were immunized with either wild-type phages (ρ) or with p195 (■), p197 (□), p217 ( ), p287 ( ) ), p335 (▲)). IgG were purified from immunized mice and tested for inhibition of $HIV_{IIIB}$ (a) or NL4-3 (b) infection in the MT2 assay (Montefiori et al., *J Clin. Microbiol.* 26:231 (1988)). Neutralization of AD8 infection was performed on PHA-activated PBMC (Montefiori el al, *J. Virol.* 72:1886 (1998)) (c). Results are expressed as percentages of protection and are representative of three independent experiments. IgG from BALB/c immunized mice gave comparable results (not shown).

Purified IgG from mice immunized with HIV-1 phagotopes exerted a significant inhibition of infection by $HIV1_{IIIB}$ and NL4-3 isolates over a wide range of IgG concentrations in an in vitro acute infection system, with 50% protection observed at IgG concentrations of 0.8 to 3 $\mu$g/ml in neutralization assays with $HIV_{IIIB}$ or NLA4-3, respectively (FIG. 5*a,b*). Consistent levels of viral neutralization were also obtained in the case of the AD8 primary isolate, with the exception of p335-specific Abs, which exerted partial protection only at the highest concentrations (FIG. 5*c*).

The selected phagotopes fulfilled the requirement for an effective immunogen. In fact, Abs from phagotope-immunized mice neutralized HIV-1 strains in vitro, suggesting that they bind well to the virus under physiologic conditions and could possibly prevent or inhibit HIV infection when induced in phagotope-immunized primates. In support of this possibility, serum Abs of SHIV-infected monkeys showed a strong reactivity with the phage-displayed epitopes. In addition, bacteriophages are excellent immunogens that induce a specific T cell dependent antibody response by parenteral as well as oral administration (Galfre et al., *Methods Enzymol.,* 267:109 (1996); Delmastro et al., *Vaccine* 15:1276 (1997)).

Example 6

Immunogenicity of epitopes in *Rhesus macaque* monkeys

An immunization trial of a cohort of *Rhesus macaque* monkeys was initiated to verify the immunogenic properties of the HIV-1 specific epitopes selected by screening the Random Peptide Libraries displayed on phage as described in the examples above and in *J. Immunol.* 162:6155 (1999). To this end, three groups of five animals were immunized with a pool phage 195, 197, 217, 287, and 335 as follows: Immunization Schedule: 1 injection every 6 weeks.

Group I: Wild-type (WT) phage ($2.5\times10^{14}$ phage particles each animal/four animals total)

GroupII φ195; φ197; φ217; φ287; φ335 ($5\times10^{13}$ phage particles each animal/five animal total)

Group III φ195; φ197; φ217; φ287; φ335 ($1\times10^{13}$ phage particles each animal/five animals total)

Figure 6A:
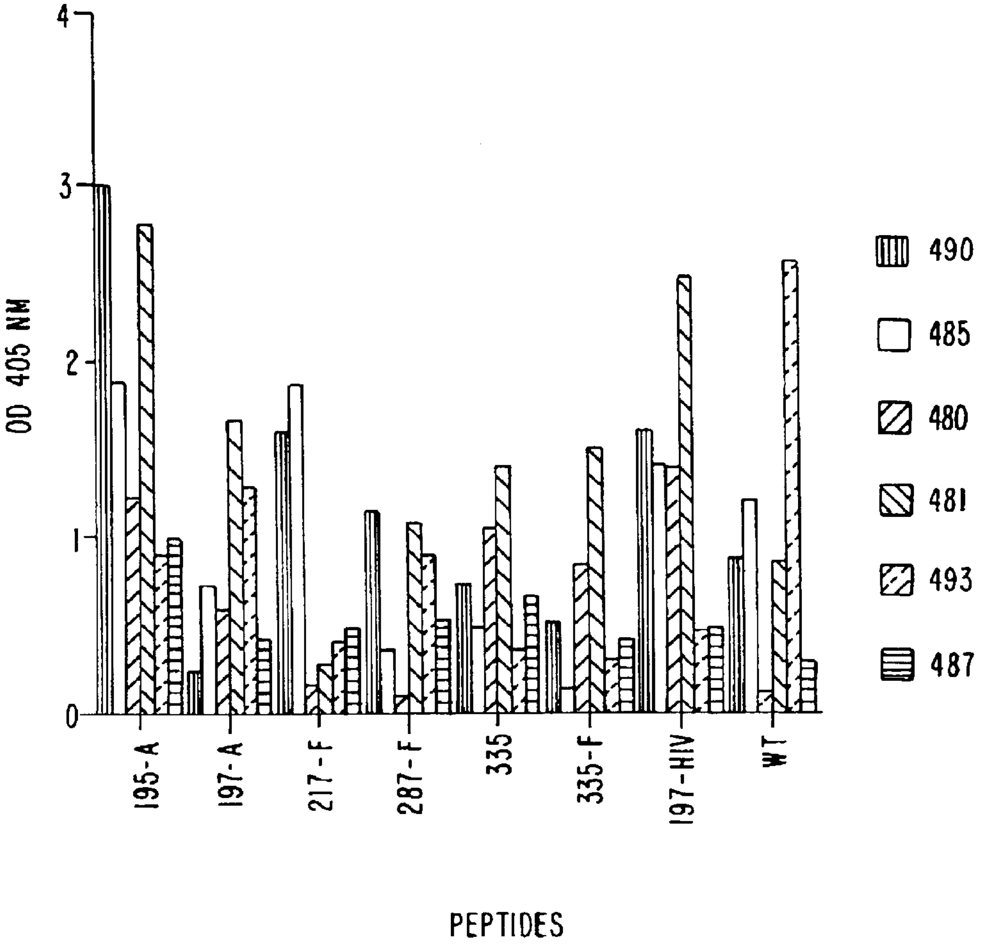
FIG. 6. ELISA reactivities of sera from *Rhesus macaque* monkeys inoculated with (a) phage-displayed epitopes or (b) WT-phage.
Figure 6B:
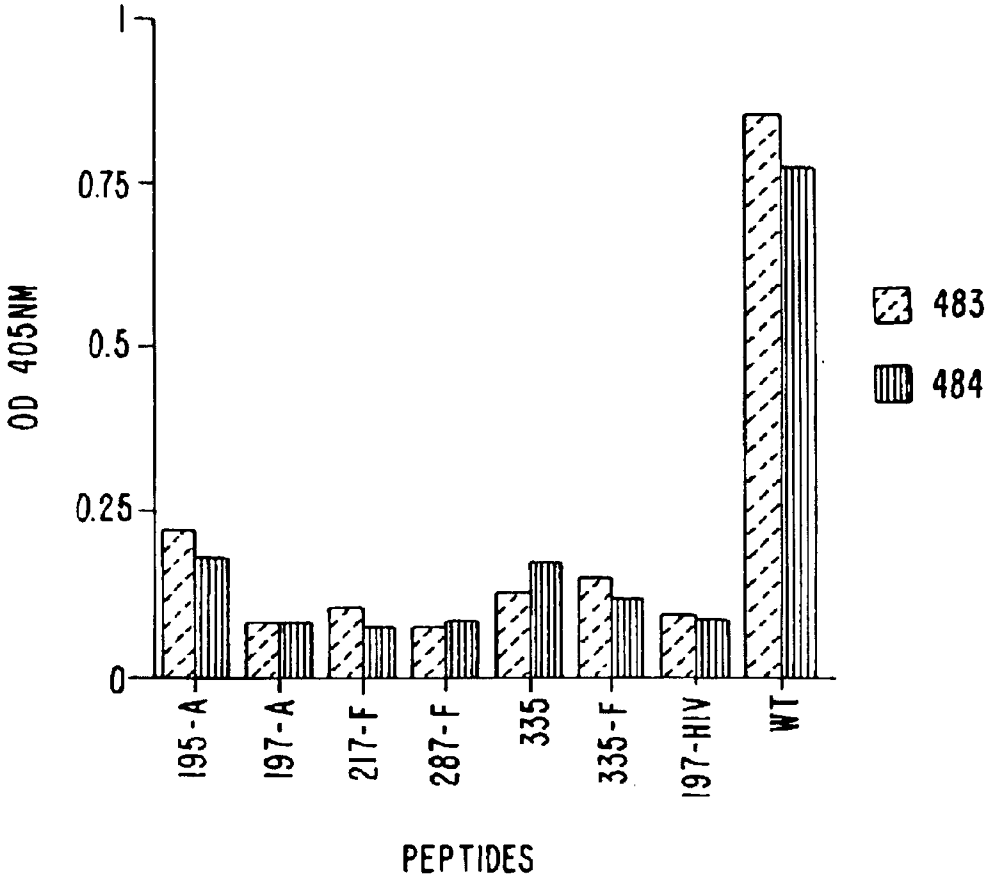

The adjuvant QS21 (Aquila Pharmaceuticals) was used in an amount of 100 $\mu$g/injection. The immunogens were injected intramuscularly at multiple sites. The plasma collected at the 4th injection (the third boost) was tested for the presence of an antibody response specific for the epitope utilized as the immunogen. Sera from either WT-phage-immunized or epitope-immunized monkeys were tested by ELISA for binding to peptides representing the original phage-displayed epitopes. As shown in FIG. 6*a*, sera from monkeys immunized with HIV-epitopes showed a substantial degree of ELISA reactivity to the different epitopes, while monkeys immunized with wt phage did not show any specific antibody response (FIG. 6*b*). These data indicate that the phagotopes originally selected from RPL are immunogenic in non-human primates and elicited a specific antibody response.

Figure 7:
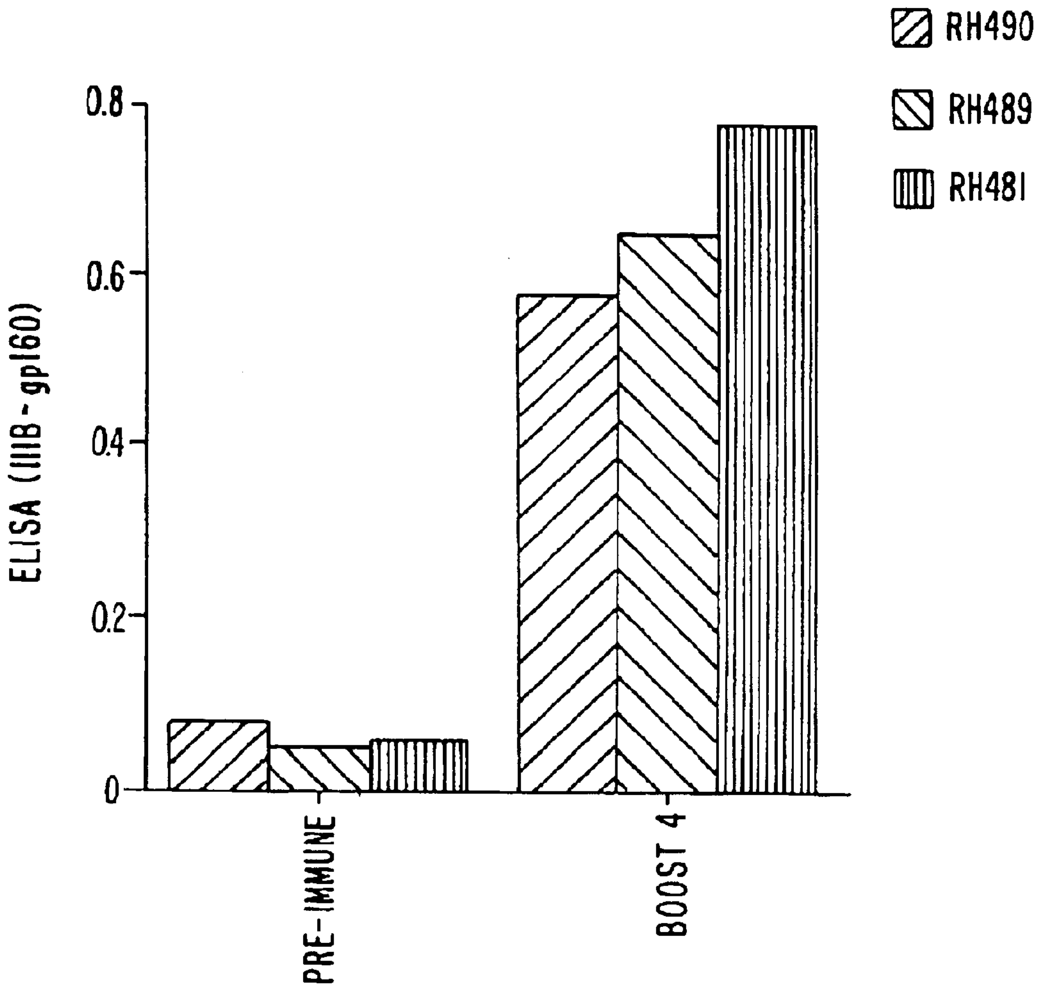
FIG. 7. ELISA reactivity of sera from *Rhesus macaque* monkeys that was assessed for binding to HIV-IIIB gp160.

Because the selected epitopes are mimotopes of discrete regions of the HIV-1 envelope, the monkey antibodies would be expected to bind to HIV-1 envelope. To test this possibility, the sera collected from the immunized monkeys were tested by ELISA for binding to HIV-IIIB gp 160. As shown in FIG. 7, serum antibodies from three animals tested positive in ELISA. The above results indicated that epitopes selected from RPL for their binding to antibodies of HIV-positive subjects function as antigenic mimics of discrete regions of HIV-1 proteins.

Example 7

Engineered peptide epitopes

The peptide sequences present on phagotopes 195, 197, 217, 287 and 335 were also modified to obtain peptide epitopes capable of functioning as antigenic and immunogenic mimics of the original epitopes displayed on the phages. The modifications were generated by randomly changing the number of residues flanking the core sequence previously identified, and/or by subjecting the core sequence to amino acid substitutions until the resulting peptides were found to exhibit ELISA reactivities similar to that of the original peptides displayed on the phagotopes. The amino acid sequences of modifed peptides generated in this manner are as follows:

P195 analog: EGEFCKSSGKLISLCGDPAK (SEQ ID NO: 14)

P197 analog: EGEFCQTKLVCFAAAGDPAK (SEQ ID NO:15)

P217 analog: EGEFCCNGRLYCQPCGDPAK (SEQ ID NO:16)

P287 analog: EGEFCCAGQLTCSVCGDPAK (SEQ ID NO: 17)

P335 analog: CSGRLYCHESWC (SEQ ID NO:18)

P54 analog: TKTLIYQGA (SEQ ID NO:19)

The engineered eptiopes are then determined to be immunogenic as described in Example 4–6.

Taken together, our results as demonstrated in the Examples indicate that a collection of HIV-1 mimotopes can be retrieved from combinatorial phage libraries by taking advantage of the specific antibody repertoire induced by natural infection, and thus are useful in the development of effective HIV-1 vaccines.

What is claimed is:

1. An antigenic peptide of less than 100 amino acids having an antigenic subsequence comprising X-KSSGKLISL-X (SEQ ID NOS: 1 and 31), wherein X is independently an amino acid or sequence of amino acids with the proviso that X is not identical to the amino acid or amino acids naturally flanking the subsequences in human immunodeficiency virus-1 (HIV-1).

2. An antigenic peptide of claim 1, wherein the antigenic subsequence is EGEFCKSSGKLISLCGDPAK (SEQ ID NO: 14).

3. A peptide of claim 1, wherein the antigenic subsequence comprises an antigenic determinant that does not give rise to HIV-1-specific antibodies to more than twelve other antigenic determinants on HIV-1.

4. A method for raising antibodies against HIV-1, said method comprising administering to an animal an amount of an antigenic peptide having an antigenic subsequence comprising X-KSSGKLISL-X (SEQ ID NOS: 1 and 31), wherein X is independently an amino acid or sequence of amino acids with the proviso that X is not identical to the amino acid or amino acids naturally flanking the subsequences in HIV-1, and further wherein the composition does not give rise to_HIV-1-specific antibodies to more than twelve other antigenic determinants on HIV-1, said amount sufficient to raise antibodies in the animal.

5. The method of claim 4, wherein the antigenic subsequence is EGEFCKSSGKLISLCGDPAK SEQ ID NO: 14).

6. A method for detecting HIV-1-specific antibodies in a person suspected of being infected with HIV-1, said method comprising the step of incubating a biological sample from the person with an antigenic peptide having an antigenic subsequence comprising X-KSSGKLISL-X SEQ ID NOS: 1 and 31) in an amount sufficient to detect the presence of antibodies which bind to the antigenic determinant and determining the binding of the antibody to the antigenic determinant.

7. The method of claim 6, wherein the antigenic subsequence is EGEFCKSSGKLISLCGDPAK (SEQ ID NO: 14).

* * * * *

SEQUENCE LISTING

<160> NUMBER OF SEQ ID NOS: 34

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence:antigenic
determinant peptide
<221> NAME/KEY: MOD_RES
<222> LOCATION: (1)
<223> OTHER INFORMATION: Xaa = any amino acid not identical to the amino
acid naturally flanking the subsequence at positions
2-10 in HIV-1
<221> NAME/KEY: MOD_RES
<222> LOCATION: (11)
<223> OTHER INFORMATION: Xaa = any amino acid not identical to the amino
acid naturally flanking the subsequence at positions
2-10 in HIV-1

<400> SEQUENCE: 1

Xaa Lys Ser Ser Gly Lys Leu Ile Ser Leu Xaa
1 5 10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence:antigenic
determinant peptide
<221> NAME/KEY: MOD_RES
<222> LOCATION: (1)
<223> OTHER INFORMATION: Xaa = any amino acid not identical to the amino
acid naturally flanking the subsequence at positions
2-10 in HIV-1
<221> NAME/KEY: MOD_RES
<222> LOCATION: (11)
<223> OTHER INFORMATION: Xaa = any amino acid not identical to the amino
acid naturally flanking the subsequence at positions
2-10 in HIV-1

<400> SEQUENCE: 2

Xaa Cys Asn Gly Arg Leu Tyr Cys Gly Pro Xaa
1 5 10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence:antigenic
determinant peptide
<221> NAME/KEY: MOD_RES
<222> LOCATION: (1)
<223> OTHER INFORMATION: Xaa = any amino acid not identical to the amino
acid naturally flanking the subsequence at positions
2-10 in HIV-1
<221> NAME/KEY: MOD_RES
<222> LOCATION: (11)
<223> OTHER INFORMATION: Xaa = any amino acid not identical to the amino
acid naturally flanking the subsequence at positions
2-10 in HIV-1

<400> SEQUENCE: 3

Xaa Gly Thr Lys Leu Val Cys Phe Ala Ala Xaa
1 5 10

<210> SEQ ID NO 4
<211> LENGTH: 9

-continued

```
<212> TYPE: PRT
<213> ORGANISM: Artificial Sequence
<220> FEATURE:
<223> OTHER INFORMATION: Description of Artificial Sequence:p195 epitope
      antigenic determinant peptide

<400> SEQUENCE: 4

Lys Ser Ser Gly Lys Leu Ile Ser Leu
  1               5


<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:p217 epitope
      antigenic determinant peptide

<400> SEQUENCE: 5

Cys Asn Gly Arg Leu Tyr Cys Gly Pro
  1               5


<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence:p197 epitope
      antigenic determinant peptide

<400> SEQUENCE: 6

Gly Thr Lys Leu Val Cys Phe Ala Ala
  1               5


<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence:antigenic
      determinant peptide

<400> SEQUENCE: 7

Glu Ala Thr Val Val Tyr Pro Ala Pro
  1               5


<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence:p54 epitope
      with no obvious sequence homology with HIV protein
      domains

<400> SEQUENCE: 8

Thr Lys Thr Leu Ile Tyr Gly Gly Ala
  1               5


<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence:p163 epitope
      with no obvious sequence homology with HIV protein
      domains

<400> SEQUENCE: 9
```

-continued

```
Lys Arg Ile Val Ile Gly Pro Gln Thr
  1               5


<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence:antigenic
      determinant peptide

<400> SEQUENCE: 10

Cys Cys Gly Cys Leu Thr Cys Ser Val
  1               5


<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence:antigenic
      determinant peptide

<400> SEQUENCE: 11

Ser Gly Arg Leu Tyr Cys His Glu Ser Trp
  1               5                  10


<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence:antigenic
      determinant peptide

<400> SEQUENCE: 12

Phe Ala Leu Ser His Tyr Asp Lys Pro
  1               5


<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence:p689 epitope
      with no obvious sequence homology with HIV protein
      domains

<400> SEQUENCE: 13

Arg Pro Thr Leu Arg Phe Gln Gly Ala
  1               5


<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence:p195 analog
      antigenic determinant peptide

<400> SEQUENCE: 14

Glu Gly Glu Phe Cys Lys Ser Ser Gly Lys Leu Ile Ser Leu Cys Gly
  1               5                  10                  15

Asp Pro Ala Lys
             20
```

-continued

```
<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence:p197 analog
      antigenic determinant peptide

<400> SEQUENCE: 15

Glu Gly Glu Phe Cys Gln Thr Lys Leu Val Cys Phe Ala Ala Ala Gly
  1               5                  10                  15

Asp Pro Ala Lys
             20


<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence:p217 analog
      antigenic determinant peptide

<400> SEQUENCE: 16

Glu Gly Glu Phe Cys Cys Asn Gly Arg Leu Tyr Cys Gln Pro Cys Gly
  1               5                  10                  15

Asp Pro Ala Lys
             20


<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence:p287 analog
      antigenic determinant peptide

<400> SEQUENCE: 17

Glu Gly Glu Phe Cys Cys Ala Gly Gln Leu Thr Cys Ser Val Cys Gly
  1               5                  10                  15

Asp Pro Ala Lys
             20


<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence:p335 analog
      antigenic determinant peptide

<400> SEQUENCE: 18

Cys Ser Gly Arg Leu Tyr Cys His Glu Ser Trp Cys
  1               5                  10


<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence:p54 analog
      antigenic determinant peptide

<400> SEQUENCE: 19

Thr Lys Thr Leu Ile Tyr Gln Gly Ala
  1               5
```

-continued

```
<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence:gp120 v1
      region (residues 112-120) of HIV1-U16374 primary isolate

<400> SEQUENCE: 20

Gly Thr Lys Thr Asn Asn Ser Ser Gly Lys Leu Ile Glu Leu Gly Glu
  1               5                  10                  15

Ile Lys


<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence:gp120 C2
      region (residues 198-205) of HIV1-U116077 primary isolate

<400> SEQUENCE: 21

Leu Lys Cys Asn Asp Lys Lys Phe Cys Gly Lys Gly
  1               5                  10


<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence:gp41
      (residues 602-605) of HIVANT70 primary isolate

<400> SEQUENCE: 22

Cys Lys Gly Lys Leu Val Cys Tyr Thr Ser
  1               5                  10


<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence:conserved
      gp41 domain consensus from HIV subtypes G and D

<400> SEQUENCE: 23

Ser Gly Lys His Ile Cys Thr Thr Asn
  1               5


<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence:conserved
      gp41 domain consensus from HIV subtypes F and A

<400> SEQUENCE: 24

Ser Gly Lys Leu Ile Cys Thr Thr Asn
  1               5


<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence:conserved
      gp41 domain consensus from HIV subtype E
```

-continued

<400> SEQUENCE: 25

Ser Gly Lys Ile Ile Cys Thr Thr Ala
1 5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence:conserved gp41 domain consensus from HIV subtypes C and B

<400> SEQUENCE: 26

Ser Gly Lys Leu Ile Cys Thr Thr Ala
1 5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence:p32 epitope with no obvious sequence homology with HIV protein domains

<400> SEQUENCE: 27

Glu Ala Thr Phe Val Tyr Pro Ala Pro
1 5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence:p287 epitope with no obvious sequence homology with HIV protein domains

<400> SEQUENCE: 28

Cys Ala Gly Gly Leu Thr Cys Ser Val
1 5

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence:p335 epitope with no obvious sequence homology with HIV protein domains

<400> SEQUENCE: 29

Ser Gly Arg Leu Tyr Cys His Glu Ser Trp
1 5 10

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence:p483 epitope with no obvious sequence homology with HIV protein domains

<400> SEQUENCE: 30

Phe Ala Ser Leu His Tyr Asp Lys Pro
1 5

<210> SEQ ID NO 31
<211> LENGTH: 99

-continued

<212> TYPE: PRT
<213> ORGANISM: Artificial Sequence
<220> FEATURE:
<223> OTHER INFORMATION: Description of Artificial Sequence:antigenic determinant peptide
<221> NAME/KEY: MOD_RES
<222> LOCATION: (1)..(45)
<223> OTHER INFORMATION: Xaa = any amino acid not identical to the amino acid naturally flanking the subsequence at positions 46-54 in HIV-1, may be present or absent
<221> NAME/KEY: MOD_RES
<222> LOCATION: (55)..(99)
<223> OTHER INFORMATION: Xaa = any amino acid not identical to the amino acid naturally flanking the subsequence at positions 46-54 in HIV-1, may be present or absent

<400> SEQUENCE: 31

```
Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Lys Ser Ser
         35                  40                  45

Gly Lys Leu Ile Ser Leu Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa Xaa
                 85                  90                  95

Xaa Xaa Xaa
```

<210> SEQ ID NO 32
<211> LENGTH: 99
<212> TYPE: PRT
<213> ORGANISM: Artificial Sequence
<220> FEATURE:
<223> OTHER INFORMATION: Description of Artificial Sequence:antigenic determinant peptide
<221> NAME/KEY: MOD_RES
<222> LOCATION: (1)..(45)
<223> OTHER INFORMATION: Xaa = any amino acid not identical to the amino acid naturally flanking the subsequence at positions 46-54 in HIV-1, may be present or absent
<221> NAME/KEY: MOD_RES
<222> LOCATION: (55)..(99)
<223> OTHER INFORMATION: Xaa = any amino acid not identical to the amino acid naturally flanking the subsequence at positions 46-54 in HIV-1, may be present or absent

<400> SEQUENCE: 32

```
Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Cys Asn Gly
         35                  40                  45

Arg Leu Tyr Cys Gly Pro Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa Xaa
                 85                  90                  95

Xaa Xaa Xaa
```

-continued

```
<210> SEQ ID NO 33
<211> LENGTH: 99
<212> TYPE: PRT
<213> ORGANISM: Artificial Sequence
<220> FEATURE:
<223> OTHER INFORMATION: Description of Artificial Sequence:antigenic
      determinant peptide
<221> NAME/KEY: MOD_RES
<222> LOCATION: (1)..(45)
<223> OTHER INFORMATION: Xaa = any amino acid not identical to the amino
      acid naturally flanking the subsequence at positions 46-54 in
      HIV-1, may be present or absent
<221> NAME/KEY: MOD_RES
<222> LOCATION: (55)..(99)
<223> OTHER INFORMATION: Xaa = any amino acid not identical to the amino
      acid naturally flanking the subsequence at positions 46-54 in
      HIV-1, may be present or absent

<400> SEQUENCE: 33

Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Gly Thr Lys
         35                  40                  45

Leu Val Cys Phe Ala Ala Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa Xaa
                 85                  90                  95

Xaa Xaa Xaa


<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence:gp41 epitope
      recognized by 2F5 monoclonal antibody

<400> SEQUENCE: 34

Glu Leu Asp Lys Trp Ala
  1               5
```